US010676451B2

(12) United States Patent
Teles et al.

(10) Patent No.: US 10,676,451 B2
(45) Date of Patent: Jun. 9, 2020

(54) PROCESS FOR PURIFYING PROPYLENE OXIDE

(71) Applicants: BASF SE, Ludwigshafen am Rhein (DE); Dow Global Technologies LLC, Midland, MI (US)

(72) Inventors: Joaquim Henrique Teles, Ludwigshafen (DE); Marvin Kramp, Ludwigshafen (DE); Christian Mueller, Ludwigshafen (DE); Nicolai Tonio Woerz, Ludwigshafen (DE); Bernd Metzen, Ludwigshafen (DE); Tobias Keller, Ludwigshafen (DE); Dominic Riedel, Ludwigshafen (DE); Heiner Schelling, Ludwigshafen (DE); Markus Weber, Ludwigshafen (DE); Daniel Urbanczyk, Ludwigshafen (DE); Andrei-Nicolae Parvulescu, Ludwigshafen (DE); Ulrike Wegerle, Worms (DE); Ulrich Mueller, Ludwigshafen (DE); Meinolf Weidenbach, Stade (DE); Werner J. Witzl, Stade (DE)

(73) Assignees: BASF SE, Ludwigshafen am Rhein (DE); Dow Global Technologies LLC, Midland, MI (US)

( * ) Notice: Subject to any disclaimer, the term of this patent is extended or adjusted under 35 U.S.C. 154(b) by 0 days.

(21) Appl. No.: 16/315,345

(22) PCT Filed: Jul. 19, 2017

(86) PCT No.: PCT/EP2017/068227
§ 371 (c)(1),
(2) Date: Jan. 4, 2019

(87) PCT Pub. No.: WO2018/015434
PCT Pub. Date: Jan. 25, 2018

(65) Prior Publication Data
US 2019/0322634 A1 Oct. 24, 2019

(30) Foreign Application Priority Data
Jul. 20, 2016 (EP) .................................... 16180305

(51) Int. Cl.
*C07D 301/32* (2006.01)
*B01D 3/14* (2006.01)
*C07D 303/04* (2006.01)

(52) U.S. Cl.
CPC .......... *C07D 301/32* (2013.01); *B01D 3/143* (2013.01); *C07D 303/04* (2013.01)

(58) Field of Classification Search
None
See application file for complete search history.

(56) References Cited

U.S. PATENT DOCUMENTS

| 3,149,131 | A | 9/1964 | Bartlett |
| 4,369,096 | A | 1/1983 | Seifert et al. |
| 5,693,193 | A | 12/1997 | Deguchi et al. |
| 2004/0106811 | A1 | 6/2004 | Hofen et al. |

FOREIGN PATENT DOCUMENTS

| DE | 681 866 C | 10/1939 |
| EP | 0 004 019 A2 | 9/1979 |
| EP | 0 673 935 A2 | 9/1995 |
| EP | 1 122 249 A1 | 8/2001 |
| WO | WO 2004/048355 A1 | 6/2004 |
| WO | WO 2011/006990 A1 | 1/2011 |
| WO | WO 2011/123541 A1 | 10/2011 |
| WO | WO 2015/049327 A1 | 4/2015 |

OTHER PUBLICATIONS

U.S. Appl. No. 15/509,238, filed Mar. 7, 2017, US 2017-0283352 A1, Thomas Fenlon, et al.
U.S. Appl. No. 15/509,228, filed Mar. 7, 2017, US 2017-0275225 A1, Dominic Riedel, et al.
U.S. Appl. No. 15/509,527, filed Mar. 8, 2017, US 2017-0246620 A1, Andrei-Nicolae Parvulescu, et al.
U.S. Appl. No. 15/550,581, filed Aug. 11, 2017, US 2018-0036723 A1, Dominic Riedel, et al.
U.S. Appl. No. 15/557,187, filed Sep. 11, 2017, US 2018-0044179 A1, Heiner Schelling, et al.
U.S. Appl. No. 15/316,220, filed Dec. 5, 2016, US 2018-0134570 A1, Stefan Maurer, et al.
U.S. Appl. No. 16/202,918, filed Nov. 28, 2018, Stefan Maurer, et al.
U.S. Appl. No. 14/794,955, filed Jul. 9, 2015, US 2016-0031789 A1, Lukas Schulz, et al.
U.S. Appl. No. 15/549,905, filed Aug. 9, 2017, US 2018-0022611 A1, Mathias Feyen, et al.
U.S. Appl. No. 15/752,991, filed Feb. 15, 2018, US 2018-0243691 A1, Ulrich Mueller, et al.
U.S. Appl. No. 15/518,945, filed Apr. 13, 2017, US 2017-0225959 A1, Stefan Maurer, et al.

(Continued)

*Primary Examiner* — Zinna Northington Davis
(74) *Attorney, Agent, or Firm* — Oblon, McClelland, Maier & Neustadt, L.L.P.

(57) ABSTRACT

Disclosed is a process for purifying propylene oxide. A stream S0 containing propylene oxide, acetonitrile, water, and an organic compound containing one or more of acetone and propionaldehyde is provided. Propylene oxide is separated from S0 by subjecting S0 to distillation in a first distillation unit, obtaining a gaseous top stream S1c enriched in propylene oxide, a liquid bottom stream S1a enriched in acetonitrile and water, and a side stream S1b containing propylene oxide and enriched in the carbonyl compound; reacting the carbonyl compound in S1b with an organic compound containing an amino group to obtain a reaction product; separating propylene oxide from the reaction product in a second distillation unit, obtaining a gaseous top stream S3a enriched in propylene oxide and a liquid bottoms stream S3b enriched in the reaction product; and introducing stream S3a into the first distillation unit.

21 Claims, 3 Drawing Sheets

(56) References Cited

OTHER PUBLICATIONS

Figure 1:
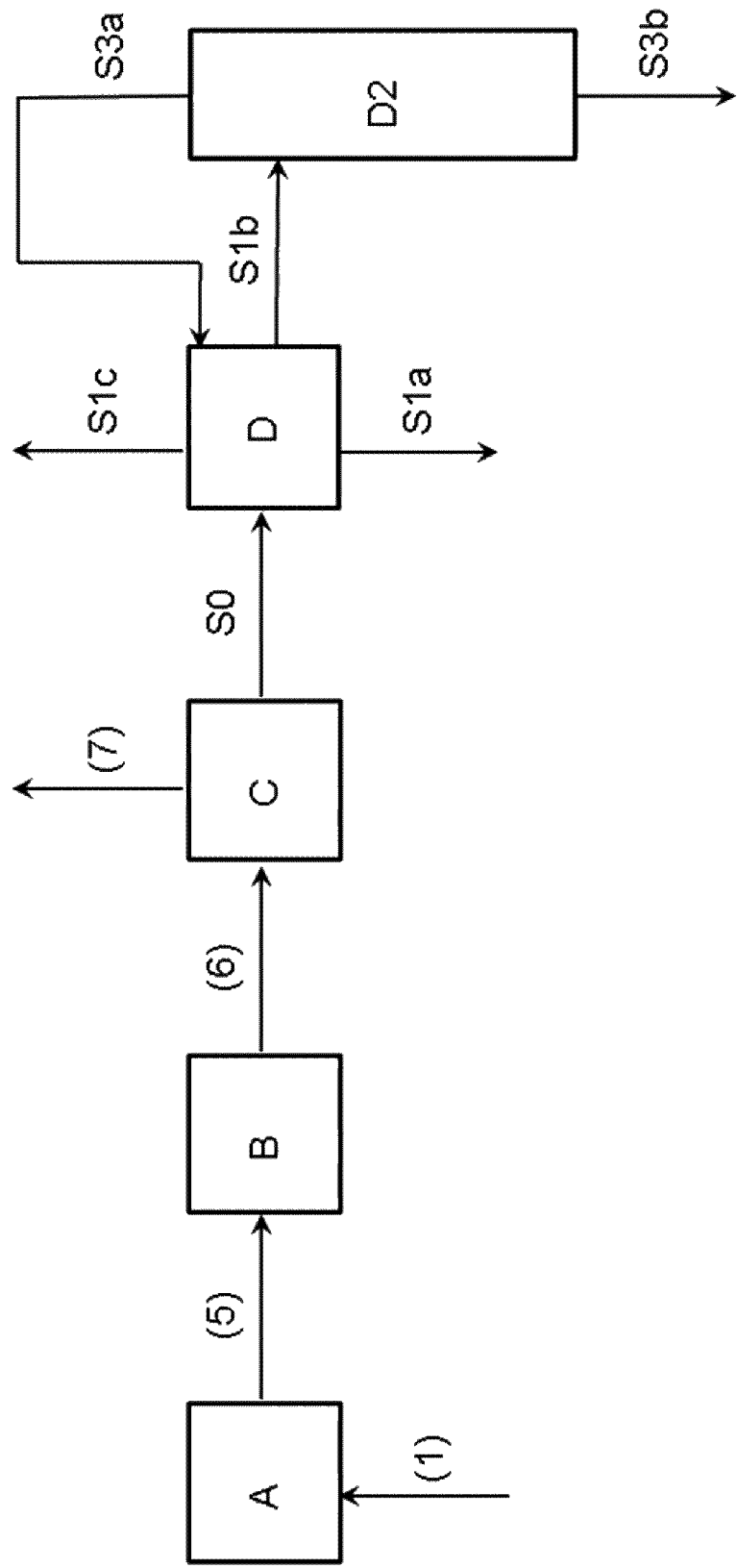

U.S. Appl. No. 15/524,484, filed May 4, 2017, US 2017-0336030 A1, Matthias Weickert, et al.
U.S. Appl. No. 15/779,218, filed May 25, 2018, US 2018-0345245 A1, Stefan Maurer, et al.
U.S. Appl. No. 15/520,129, filed Apr. 19, 2017, US 2017-0320847 A1, Nicolas Vautravers, et al.
U.S. Appl. No. 15/518,791, filed Apr. 13, 2017, US2017-0362532 A1, Ralf Pelzer, et al.
U.S. Appl. No. 14/958,207, filed Dec. 3, 2015, US 2016-0159724 A1, Nicolai Tonio Woerz, et al.
U.S. Appl. No. 15/777,931, filed May 22, 2018, US 2018-0346478 A1, Albert Werner, et al.
U.S. Appl. No. 15/514,902, filed Mar. 28, 2017, US 2018-0230076 A1, Frauke Thrun, et al.
U.S. Appl. No. 15/508,725, filed Mar. 3, 2017, US 2017-0275076 A1, Todd Edgington, et al.
U.S. Appl. No. 14/972,255, filed Dec. 17, 2015, US 2016-0176797 A1, Till Christian Brueggemann, et al.
U.S. Appl. No. 15/521,924, filed Apr. 26, 2017, US 2018-0230117 A1, Joaquim Henrique Teles, et al.
U.S. Appl. No. 14/956,800, filed Dec. 2, 2015, US 2016-0152541 A1, Yong Liu, et al.
U.S. Appl. No. 15/537,128, filed Jun. 16, 2017, US 2018-0265443 A1, Nicolas Vautravers, et al.
U.S. Appl. No. 15/744,324, filed Jan. 12, 2018, US 2018-0208532 A1, Andrei-Nicolae Parvulescu, et al.
U.S. Appl. No. 15/744,474, filed Jan. 12, 2018, US 2018-0208533 A1, Stefan Rüdenauer, et al.
U.S. Appl. No. 16/086,251, filed Sep. 18, 2018, Benedikt Kalo.
U.S. Appl. No. 15/571,107, filed Nov. 1, 2017, US 2018-0170850 A1, Nicolas Vautravers, et al.
U.S. Appl. No. 15/746,183, filed Jan. 19, 2018, US 2018-0208745 A1, Nicolas Vautravers, et al.
U.S. Appl. No. 15/779,314, filed May 25, 2018, US 2018-0333696 A1, Julia Burckhart, et al.
U.S. Appl. No. 15/746,082, filed Jan. 19, 2018, US 2018-0215724 A1, Alvaro Gordillo, et al.
U.S. Appl. No. 16/060,260, filed Jun. 7, 2018, US 2018-0362353 A1, NIcolas Vautravers, et al.
U.S. Appl. No. 16/076,600, filed Aug. 8, 2018, US 2019-0077779 A1, Dominic Riedel, et al.
U.S. Appl. No. 15/348,460, filed Nov. 10, 2016, US 2017-0129841 A1, Marco Hartmann, et al.
U.S. Appl. No. 15/766,425, filed Apr. 6, 2018, US 2018-0312458 A1, Frauke Thrun, et al.
U.S. Appl. No. 15/766,407, filed Apr. 6, 2018, US 2018-0290959 A1, Frauke Thrun, et al.
U.S. Appl. No. 15/308,730, filed Jun. 22, 2017, US 2018-0012677 A1, Roxana Haase, et al.
U.S. Appl. No. 15/348,130, filed Nov. 10, 2016, US 2017-0129840 A1, Marco Hartmann, et al.
U.S. Appl. No. 15/775,657, filed May 11, 2018, US 2018-0328601 A1, Matthias Weickert, et al.
U.S. Appl. No. 16/060,739, filed Jun. 8, 2018, US 2018-0362357 A1, Mathias Feyen, et al.
U.S. Appl. No. 16/060,229, filed Jun. 7, 2018, US 2018-0362351 A1, Andrei-Nicolae Parvulescu, et al.
U.S. Appl. No. 16/315,345, filed Apr. 4, 2019, Joaquim Henrique Teles, et al.
U.S. Appl. No. 15/348,217, filed Nov. 10, 2016, US 2017-0128916 A1, Michael Lejkowski, et al.
U.S. Appl. No. 16/073,941, filed Jul. 30, 2018, US 2019-0040005 A1, Richard Dehn, et al.
U.S. Appl. No. 16/304,511, filed Nov. 26, 2018, Mathias Feyen, et al.
U.S. Appl. No. 16/307,450, filed Dec. 5, 2018, Min-che Chen, et al.
International Search Report dated Oct. 11, 2017 in PCT/EP2017/068227 filed Jul. 19, 2017 3 pages.
International Preliminary Report on Patentability and Written Opinion dated Jan. 31, 2019 in PCT/EP2017/068227 filed on Jul. 19, 2017 8 pages.
"Hydrogen Peroxide", Ullmann's Encyclopedia Industrial Chemistry, $5^{th}$ edition, vol. A 13, 1989, pp. 443-466.

PROCESS FOR PURIFYING PROPYLENE OXIDE

The present invention is directed to a process for purifying propylene oxide, which comprises providing a stream comprising propylene oxide, acetonitrile, water, and an organic compound comprising a carbonyl group —C(=O)— to a distillation unit, wherein a side stream comprising propylene oxide is obtained, which is enriched in the carbonyl compound, which is then reacted with an organic compound comprising an amino group —NH$_2$, wherein a reaction product of the organic compound comprising a carbonyl group and the organic compound comprising an amino group is obtained; after what propylene oxide is separated from the reaction product of the organic compound comprising a carbonyl group and the organic compound comprising an amino group in a second distillation unit, wherein a gaseous top stream enriched in propylene oxide is obtained, which is introduced into the first distillation unit.

Propylene oxide is an important intermediate in the chemical industry. A suitable process for the preparation of propylene oxide starts from propene and makes use of hydrogen peroxide as oxidizing agent, acetonitrile as solvent and an epoxidation catalyst comprising a titanium zeolite. Due to its importance for industrial-scale processes, it is desired to carry out the epoxidation reaction as efficiently as possible and to purify the propylene oxide to a high degree. The epoxidation reaction results in a mixture comprising acetonitrile, water, propylene oxide and side products, for example, organic compound comprising a carbonyl group —C(=O)— (carbonyl compound) such as acetone, propionaldehyde. Especially these compounds such as acetone, propionaldehyde, which have a boiling point higher than the boiling point of propylene oxide and lower than the boiling point of the azeotropic mixture of acetonitrile and water, are challenging when it comes to separating them from the propylene oxide.

Methods for the purification of propylene oxide containing streams, which are contaminated with carbonyl compounds, are known, wherein several methods are based on a chemical binding of the carbonyl compound.

EP 0 004 019 A2 describes the separation of propylene oxide from a mixture containing up to 2 weight-% of a carbonyl compound which has 1 to 5 carbon atoms. The propylene epoxide is introduced into the middle section of a distillation unit. Above the feed point, a compound having one or more NH$_2$-groups is added to the same distillation unit. The propylene oxide depleted of the carbonyl compounds is then taken off at the head of the distillation unit. The preferred compound having one or more NH$_2$-groups is hydrazine, which is applied pure or in aqueous solution. The compound having one or more NH$_2$-groups reacts with the carbonyl group of the carbonyl compound wherein azines and hydrazones having high boiling points are formed, which can afterwards easily be separated from the propylene oxide.

Even if this method works well, it is afflicted with two problems:

The azines, hydrazones formed and unreacted hydrazine remain in the sump of the distillation unit, together with water and solvent. The follow-up separation of water and solvent by distillation leaves azines, hydrazones formed and unreacted hydrazine as high boilers in the waste water stream. Since azines, hydrazones and hydrazine are toxic, they are only tolerated in the feed stream to biological wastewater treatment plants in low concentrations of normally 50-100 ppm. Thus, the waste water stream has to be subjected to further treatments in order to eliminate these compounds before the waste water stream reaches the plant. The treatment may be a hydrogenation, which transforms hydrazine as well as azines/hydrazones into ammonia, or a suitable oxidation, for example, with hydrogen peroxide or ozone.

If the solvent is not recycled by distillation but separated by phase separation, such as described in WO 2011/006990 A, a risk remains that the azines/hydrazones enter the organic phase and thus are recycled together with the solvent to the epoxidation reactor, where undesired side reactions and, in the most extreme case, a damage of the epoxidation catalyst may be caused.

WO 2011/123541 A1 discloses the removal of ppm-amounts of aldehyde compounds from propylene oxide by ion exchange resins containing amino groups. Said method however has the disadvantage that the ion exchange resin which has to be used in stoichiometric amounts has a low amount of NH$_2$-groups thus resulting in a high consume of expensive ion exchange resin.

One problem associated with all known methods based on reactions with NH$_2$-groups is that the methods are only able to separate all compounds with carbonyl groups contained in the propylene oxide stream, without any distinction among them. This means that carbonyl compounds are separated, which are easy separable such as acetaldehyde and formaldehyde, but also propionaldehyde and acetone as well as carbonyl compounds which are hard to separate. Thus, the reagent has to be applied in much higher amounts than needed for the real separation task.

It was an object of the present invention to provide a process for the purification of propylene oxide which is efficient, uses reagents in low amounts and allows to essentially avoid the accumulation of reagents and the reaction products of carbonyl compounds with trapping reagents in the recycling acetonitrile solvent stream.

Surprisingly, it was found that for the separation of carbonyl compounds from propylene oxide, i.e. for the purification of propylene oxide, disadvantages can be avoided by subjecting a side stream from a propylene oxide distillation unit (first distillation unit) to a treatment with an organic compound comprising an amino group —NH$_2$, combined with a distillation in a second distillation unit and recycling a propylene containing top stream from the second distillation unit to the first distillation unit. For the carbonyl compounds which were found to be critical, it was surprisingly found that they could be separated selectively from the gaseous top stream of the first distillation unit, which is enriched in propylene oxide, very efficient without causing a pollution with the organic compound comprising an amino group —NH$_2$ or its reaction products with carbonyl compounds of the liquid bottoms stream from said first distillation unit, which is enriched in acetonitrile and water.

Therefore, the present invention relates to a process for purifying propylene oxide, comprising
  (i) providing a stream S0 comprising propylene oxide, acetonitrile, water, and an organic compound comprising a carbonyl group —C(=O)—, wherein said organic compound comprising a carbonyl group —C(=O)— (carbonyl compound) comprises one or more of acetone and propionaldehyde;
  (ii) separating propylene oxide from the stream S0 by distillation, comprising
    (ii.1) subjecting the stream S0 to distillation conditions in a first distillation unit, obtaining a gaseous top stream S1c which is enriched in propylene oxide compared to the stream S0, a liquid bottoms stream S1a which is enriched in acetonitrile and water compared to the stream S0, and a side stream S1b comprising propylene oxide which is enriched in the carbonyl compound compared to the stream S0;
(ii.2) reacting the carbonyl compound comprised in the side stream S1b with an organic compound comprising an amino group —NH$_2$ obtaining a reaction product of the organic compound comprising a carbonyl group and the organic compound comprising an amino group;
(ii.3) separating propylene oxide from the reaction product of the organic compound comprising a carbonyl group and the organic compound comprising an amino group in a second distillation unit, obtaining a gaseous top stream S3a which is enriched in propylene oxide and a liquid bottoms stream S3b which is enriched in the reaction product of the organic compound comprising a carbonyl group and the organic compound comprising an amino group;
(ii.4) introducing the top stream S3a which is enriched in propylene oxide propylene oxide into the first distillation unit.

Step (ii.2)

According to (ii.2), the carbonyl compound comprised in the side stream S1b is reacted with an organic compound comprising an amino group —NH$_2$, wherein a reaction product of the organic compound comprising a carbonyl group and the organic compound comprising an amino group is obtained.

Therefore, in one embodiment, the process of the present invention comprises
(i) providing a stream S0 comprising propylene oxide, acetonitrile, water, and an organic compound comprising a carbonyl group —C(=O)—, wherein said organic compound comprising a carbonyl group —C(=O)— comprises one or more of acetone and propionaldehyde;
(ii) separating propylene oxide from the stream S0 by distillation, comprising
(ii.1) subjecting the stream S0 to distillation conditions in a first distillation unit, obtaining a gaseous top stream S1c which is enriched in propylene oxide compared to the stream S0, a liquid bottoms stream S1a which is enriched in acetonitrile and water compared to the stream S0, and a side stream S1b comprising propylene oxide which is enriched in the carbonyl compound compared to the stream S0;
(ii.2) admixing the side stream S1b with an organic compound comprising an amino group —NH$_2$ and reacting the organic compound comprising a carbonyl group with the organic compound comprising an amino group, obtaining a stream S2 comprising propylene oxide and a reaction product of the organic compound comprising a carbonyl group and the organic compound comprising an amino group;
(ii.3) subjecting the stream S2 to distillation conditions in a second distillation unit, obtaining a gaseous top stream S3a which is enriched in propylene oxide compared to the stream S2, and a liquid bottoms stream S3b which is enriched in the reaction product of the organic compound comprising a carbonyl group and the organic compound comprising an amino group compared to the stream S2;
(ii.4) introducing the stream S3a into the first distillation unit.

In another embodiment, the process of the present invention comprises
(i) providing a stream S0 comprising propylene oxide, acetonitrile, water, and an organic compound comprising a carbonyl group —C(=O)—, wherein said organic compound comprising a carbonyl group —C(=O)— comprises one or more of acetone and propionaldehyde;
(ii) separating propylene oxide from the stream S0 by distillation, comprising
(ii.1) subjecting the stream S0 to distillation conditions in a first distillation unit, obtaining a gaseous top stream S1c which is enriched in propylene oxide compared to the stream S0, a liquid bottoms stream S1a which is enriched in acetonitrile and water compared to the stream S0, and a side stream S1b comprising propylene oxide which is enriched in the carbonyl compound compared to the stream S0;
(ii.2) subjecting the side stream S1b to distillation conditions in a second distillation unit and adding an organic compound comprising an amino group —NH$_2$ to the second distillation unit, preferably at the top of the second distillation unit, and reacting the organic compound comprising a carbonyl group with the organic compound comprising an amino group, obtaining a reaction product of the organic compound comprising a carbonyl group and the organic compound comprising an amino group, and obtaining a gaseous top stream S3a which is enriched in propylene oxide compared to the stream S1b, and a liquid bottoms stream S3b which is enriched in the reaction product of the organic compound comprising a carbonyl group and the organic compound comprising an amino group compared to the stream S1b;
(ii.3) introducing the stream S3a into the first distillation unit.

Stream S0

According to step (i), a stream S0 is provided which comprises propylene oxide, acetonitrile, water, and an organic compound comprising a carbonyl group —C(=O)—, wherein said organic compound comprising a carbonyl group —C(=O)— comprises one or more of acetone and propionaldehyde. Preferably, the organic compound comprising a carbonyl group —C(=O)— is a reaction product from the epoxidation of propylene with hydrogen peroxide. Generally, there are no specific restrictions what further organic compound comprising a carbonyl group —C(=O)— is comprised besides one or more of acetone and propionaldehyde. Preferably, the organic compound comprising a carbonyl group —C(=O)— further comprises, i.e. in addition to one or more of acetone and propionaldehyde, one or more further aldehydes, one or more further ketones, or a mixture of one or more further aldehydes and one or more further ketones. More preferably, the organic compound comprising a carbonyl group —C(=O)— further comprises, i.e. in addition to one or more of acetone and propionaldehyde, one or more of acetaldehyde, formaldehyde, butyraldehyde, isobutyraldehyde, 2-butanon, 1-pentanal, 2-pentanon, 3-pentanon, 2-methylpentanone, preferably one ore more of acetaldehyde, formaldehyde, butyraldehyde, isobutyraldehyde, more preferably at least acetaldehyde.

Generally, the composition of the stream S0 provided in (i) is not subject to any specific restrictions. Preferably, at least 95 weight-%, preferably at least 98 weight-%, more preferably at least 99 weight-% of the stream S0 consist of propylene oxide, acetonitrile, water, and the organic compound comprising a carbonyl group. Preferably, the stream S0 comprises the propylene oxide in amount of from 8 to 18 weight-%, more preferably from 9 to 14 weight-%, based on the total weight of the stream S0; the acetonitrile in an amount of from 60 to 75 weight-%, more preferably from 65 to 70 weight-%, based on the total weight of the stream S0; the water in amount of from 10 to 25 weight-%, more preferably from 17 to 21 weight-%, based on the total weight of the stream S0; propionaldehyde in an amount of from 10 to 1000 weight-ppm, more preferably from 30 to 500 weight-ppm, based on the total weight of the stream S0; acetone in an amount of from 50 to 400 weight-ppm, more preferably from 60 to 120 weight-ppm, based on the total weight of the stream S0; and acetaldehyde in an amount of from 80 to 300 weight-ppm, more preferably from 100 to 200 weight-ppm, based on the total weight of the stream S0.

First Distillation Unit D

According to (ii.1), the stream S0 is subjected to distillation conditions in a first distillation unit D, wherein a gaseous top stream S1c which is enriched in propylene oxide compared to the stream S0, a liquid bottoms stream S1a which is enriched in acetonitrile and water compared to the stream S0, and a side stream S1b comprising propylene oxide which is enriched in the carbonyl compound compared to the stream S0, are obtained. Generally, there is no specific restriction with respect to the design of the first distillation unit D, provided that is suitable for carrying out the separation of propylene oxide and for obtaining a side stream S1b. Preferably, the first distillation unit D employed in (ii.1) is at least one distillation tower, more preferably one distillation tower, wherein the distillation tower has preferably from 40 to 200, more preferably from 45 to 100, more preferably from 50 to 90, theoretical trays.

Preferably, the rectifying section of the first distillation unit D employed in (ii.1) consists of from 40 to 60% of the theoretical trays and the stripping section of the distillation unit D consists of from 60 to 40% of the theoretical trays.

This first distillation unit D is preferably operated at conditions allowing for obtaining a side stream S1b comprising propylene oxide which is enriched in the carbonyl compound compared to the stream S0. Preferably, the first distillation unit D employed in (ii.1) is operated at a top pressure of from 0.1 to 2.0 bar, more preferably of from 0.2 to 1.0 bar, more preferably of from 0.3 to 0.8 bar. Preferably, the first distillation unit D employed in (ii.1) is operated at a top temperature in the range of from 50 to 70° C., more preferably of from 52 to 68° C., more preferably of from 54 to 64° C.

Preferably, the first distillation unit D employed in (ii.1) is operated at an internal reflux ratio in the range of from 1 to 10, more preferably from 2 to 8, more preferably from 3 to 6.

Stream S1b

According to (ii.1) a side stream S1b comprising propylene oxide, which is enriched in the carbonyl compound compared to the stream S0, is obtained. Generally, no restrictions exists where the side stream S1b is removed from the first distillation unit as long as it comprises propylene oxide and is enriched in the carbonyl compound compared to the stream S0. Preferably, the side stream S1b obtained in (ii.1) is removed from the rectifying section of the first distillation unit. More preferably, the side stream S1b obtained in (ii.1) is removed from the rectifying section of the first distillation unit at a position which is at least 1 theoretical tray above the stripping section of the first distillation unit, more preferably from the rectifying section of the first distillation unit at a position which is from 1 to 15, preferably from 1 to 12, more preferably from 1 to 10, theoretical tray above the stripping section of the first distillation unit.

Generally, no restrictions exists regarding the composition of the side stream S1b provided that it comprises propylene oxide and is enriched in the carbonyl compound compared to the stream S0. Said organic compound comprising a carbonyl group —C(=O)— comprises one or more of acetone and propionaldehyde. In other words, side stream S1b comprises propylene oxide and is enriched in the carbonyl compound, which comprises one or more of acetone and propionaldehyde. Preferably, the organic compound comprising a carbonyl group —C(=O)— comprises further, i.e. in addition to one or more of acetone and propionaldehyde, one or more further aldehydes, one or more further ketones, or a mixture of one or more further aldehydes and one or more further ketones. In other words, the stream S1b is further enriched, i.e. in addition to being enriched in one or more of acetone and propionaldehyde in one or more further aldehydes, one or more further ketones, or a mixture of one or more further aldehydes and one or more further ketones. More preferably, the side stream S1b obtained in (ii.1) comprising propylene oxide and being enriched in the carbonyl compound compared to the stream S0 is further enriched, i.e. in addition to being enriched in one or more of acetone and propionaldehyde, in one or more of acetaldehyde, formaldehyde, butyraldehyde, isobutyraldehyde, 2-butanon, 1-pentanal, 2-pentanon, 3-pentanon, 2-methylpentanone, preferably one ore more of acetaldehyde, formaldehyde, butyraldehyde, isobutyraldehyde, more preferably at least in acetaldehyde.

Preferably, at least 95 weight-%, preferably at least 98 weight-%, more preferably at least 99 weight-% of the stream S1b consist of propylene oxide, acetonitrile, water, and the organic compound comprising a carbonyl group.

Preferably, the stream S1b comprises the propylene oxide in an amount of from 68 to 96 weight-%, preferably from 70 to 95 weight-%, based on the total weight of the stream S1b; the acetonitrile in an amount of from 2 to 25 weight-%, preferably from 3.5 to 22 weight-%, based on the total weight of the stream S1b; the organic compound comprising a carbonyl group in an amount of from 0.05 to 4 weight-%, preferably from 0.1 to 2.6 weight-%; based on the total weight of the stream S1b; wherein the organic compound comprising a carbonyl group preferably comprises propionaldehyde in an amount of from 0.03 to 3 weight-%, preferably from 0.05 to 2.0 weight-%, based on the total weight of the stream S1b, and acetone in an amount of from 0.01 to 1.0 weight-%, preferably from 0.02 to 0.6 weight-%, based on the total weight of the stream S1b, and acealdehyde in an amount of from 0.01 to 0.5 weight-%, preferably from 0.03 to 0.1 weight-%, based on the total weight of the stream S1b.

Organic Compound Comprising an Amino Group —NH$_2$

According to (ii.2), the carbonyl compound comprised in the side stream S1b is reacted with an organic compound comprising an amino group —NH$_2$ wherein a reaction product of the organic compound comprising a carbonyl group and the organic compound comprising an amino group is obtained. Generally, no restrictions exists with respect to the organic compound comprising an amino group —NH$_2$ provided that a reaction with the carbonyl compound occurs. Preferably, the organic compound comprising an amino group —NH$_2$ comprises one or more of R—NH$_2$, wherein R is a substituted or unsubstituted, branched or unbranched C1-C5-alkyl, preferably selected from the group consisting of ethyl amine, n-propyl amine, iso-propyl amine, n-butyl amine, iso-butyl amine, ethanol amine; R1-NH$_2$, wherein R1 is a C6-C10-aryl group with at least one further substituent R2 selected from the group consisting of hydrogen, —CH$_3$, —NO$_2$ positioned at the aryl group, preferably selected from the group consisting of aniline, toluidine, ortho-nitroaniline, alpha-naphthylamine, beta-naphthylamine; NH$_2$—R3-NH$_2$, wherein R3 is selected from the group consisting of C2-C3-alkylene groups or phenyl, preferably selected from the group consisting of 1,2-diamino ethane, 1,2-diamino propane, 1,3-diamino propane, 1,2-diamino benzene, 1,3-diamino benzene, 1,4-diamino benzene; N—C1-C6-aminales; carbonic acid amides, preferably selected from the group consisting of acetamide, propanamide, iso-butyramide, benzene sulfonamide, para-toluenesulfonamide; amide of the mono-methylester of methylphosphonic acid; amides of carbonic acids, preferably selected from the group consisting of urea, N—C1-C6-alkyl urea, N,N'—C1-C6-dialkyl urea; amino acids, preferably selected from the group consisting of glycine, alanine, norvaline, methionine, valine, lysine; anthranilic acid; nitriles of alpha-amino carbonic acids, preferably alpha-amino-propionitrile; cyanamide; hydroxylamine; O-methyl-hydroxylamine; hydroxylamine-O-sufonic acid; hydrazine; hydrazine monohydrate; monoC1-C4-alkyl hydrazines, preferably selected from the group consisting of methyl hydrazine, ethyl hydrazine, propyl hydrazine, butyl hydrazine, iso-propyl hydrazine; aryl hydrazines, preferably selected from the group consisting of phenylhydrazine, 2,4-dinitrophenylhydrazine; dialkyl hydrazines, preferably N,N-dimethyl hydrazine; hydrazides, preferably selected from the group consisting of semi carbazide, acethydrazide, benzoic acid hydrazide, iso-butanoic acid hydrazide; and hydrazides of thiocarbonic acids of the formula R4(S=O)$_2$—NH—NH$_2$ wherein R4 is selected from the group consisting of C6-C10-aryl and C1-C6-alkyl; wherein the organic compound comprising an amino group —NH$_2$ preferably comprises hydrazine, more preferably hydrazine.

Generally, there are no specific restrictions how the organic compound comprising an amino group —NH$_2$ is used provided that it is capable of reacting with the carbonyl compound. Preferably, the organic compound comprising an amino group —NH$_2$ is used solid or dissolved, more preferably dissolved in a solvent comprising water, more preferably dissolvent in water.

Generally, there are no specific restrictions what amount of the organic compound comprising an amino group —NH$_2$ is used provided that it is suitable for reacting with the carbonyl compound. Preferably, the molar ratio of the molar amount of amino groups —NH$_2$ comprised in the organic compound comprising an amino group —NH$_2$ used or admixed in (ii.2) to the molar amount of carbonyl groups comprised in the organic compound comprising a carbonyl group is in the range of from 0.5:1 to 100:1, preferably from 0.75:1 to 25:1, more preferably from 1:1 to 10:1.

Reactor

According to one embodiment, the carbonyl compound comprised in the side stream S1$b$ is reacted in (ii.2) with an organic compound comprising an amino group —NH$_2$ obtaining a reaction product of the organic compound comprising a carbonyl group and the organic compound comprising an amino group. Preferably, the reacting of the organic compound comprising a carbonyl group with the organic compound comprising an amino group in (ii.2) is done in one or more reactors, preferably in one reactor. Generally, there are no specific restrictions regarding the design of the reactor provided that it is suitable for carrying out the reaction of the carbonyl compound with the organic compound comprising an amino group —NH$_2$. Preferably, the reactor is a continuous reactor, more preferably the reactors is a continuous flow stirred-tank reactor (CSTR), stirred tank battery, tube reactor or a combination of two or more of these reactors, more preferably a tube reactor.

Preferably, the side stream S1$b$ and a stream comprising the organic compound comprising an amino group —NH$_2$ are passed into the reactor. Generally, there are no specific restrictions regarding the admixing of the streams, provided that it is suitable for carrying out the reaction of the carbonyl compound with the organic compound comprising an amino group —NH$_2$. Preferably, if the organic compound comprising an amino group —NH$_2$ is used dissolved, preferably dissolved in a solvent comprising water, more preferably dissolvent in water, the admixing of the stream comprising the organic compound comprising an amino group —NH$_2$ and the side stream S1$b$ comprising the carbonyl compound is done so that only one liquid phase is formed.

Generally, there are no specific restrictions regarding the residence time in the reactor, provided that is suitable for carrying out the reaction of the carbonyl compound with the organic compound comprising an amino group —NH$_2$. Preferably, the residence time for reacting the organic compound comprising a carbonyl group with the organic compound comprising an amino group in (ii.2) is at least 0.1 h, more preferably from 0.3 to 2.0 h.

Generally, there are no specific restrictions regarding the reaction temperature, provided that is suitable for carrying out the reaction of the carbonyl compound with the organic compound comprising an amino group —NH$_2$. Preferably, the organic compound comprising a carbonyl group is reacted with the organic compound comprising an amino group in (ii.2) at a temperature in the range of from 10 to 80° C., preferably from 20 to 60° C.

Second Distillation Unit D2

According to (ii.3), propylene oxide is separated from the reaction product of the organic compound comprising a carbonyl group and the organic compound comprising an amino group in a second distillation unit D2, obtaining a gaseous top stream S3$a$ which is enriched in propylene oxide and a liquid bottoms stream S3$b$ which is enriched in the reaction product of the organic compound comprising a carbonyl group and the organic compound comprising an amino group.

Generally, there is no specific restriction with respect to the design of the second distillation unit D2, provided that is suitable for carrying out the separation of gaseous top stream S3$a$ which is enriched in propylene oxide and liquid bottoms stream S3$b$ which is enriched in the reaction product of the organic compound comprising a carbonyl group and the organic compound comprising an amino group. Preferably, the second distillation unit employed in (ii.3) is at least one distillation tower, more preferably one distillation tower, wherein the distillation tower has preferably at least 5, more preferably from 5 to 25, more preferably from 8 to 20, theoretical trays. Preferably, the rectifying section of the second distillation unit employed in (ii.3) consists of from 90 to 100%, preferably from 95 to 100%, more preferably from 99 to 100%, of the theoretical trays.

Generally, there is no specific restriction with respect to the pressure at which the second distillation unit D2 is operated, provided that is suitable for carrying out the separation of gaseous top stream S3$a$ which is enriched in propylene oxide and liquid bottoms stream S3$b$ which is enriched in the reaction product of the organic compound comprising a carbonyl group and the organic compound comprising an amino group. Preferably, the second distillation unit employed in (ii.3) is operated at a top pressure of from 0.1 to 2.0 bar, more preferably of from 0.2 to 1.0 bar, more preferably of from 0.3 to 0.8 bar.

Generally, there is no specific restriction with respect to the temperature at which the second distillation unit D2 is operated, provided that is suitable for carrying out the separation of gaseous top stream S3a which is enriched in propylene oxide and liquid bottoms stream S3b which is enriched in the reaction product of the organic compound comprising a carbonyl group and the organic compound comprising an amino group. Preferably, the first distillation unit employed in (ii.1) is operated at a bottoms temperature in the range of from 30 to 50° C., more preferably of from 32 to 45° C., more preferably of from 36 to 40° C.

Liquid bottoms stream S3b which is enriched in the reaction product of the organic compound comprising a carbonyl group and the organic compound comprising an amino group can be sent to the flare for disposal or can be passed to an acetonitrile recovery unit.

Gaseous top stream S3a is enriched in propylene oxide and depleted of the organic compound comprising a carbonyl group compared to side stream S1b.

Re-Introduction of S3a

According to (ii.4), the top stream S3a obtained from the second distillation unit D2, which is enriched in propylene oxide, is introduced into the first distillation unit. Preferably, the gaseous top stream S3a obtained in (ii.3) is introduced into the first distillation unit in (ii.4) in the rectifying section of the first distillation unit at a position which is at least 1 theoretical tray above the stripping section of the first distillation unit, more preferably at a position which is from 1 to 15, preferably from 1 to 12, more preferably from 1 to 10, theoretical tray above the stripping section of the first distillation unit. Preferably, the gaseous top stream S3a obtained in (ii.3) is introduced into the first distillation unit in (ii.4) in the rectifying section of the first distillation unit at a position which is 0 to 3 theoretical trays, more preferably 0 theoretical trays above the theoretical tray where the side stream S1b obtained in (ii.1) is removed from the rectifying section of the first distillation unit.

Stream S1a

According to (ii.1), a liquid bottoms stream S1a is obtained from the first distillation unit, which is enriched in acetonitrile and water compared to the stream S0. Preferably, at least 95 weight-% of S1a consist of acetonitrile and water, wherein preferably, the weight ratio of acetonitrile relative to water in the stream S1a is greater than 1:1. Preferably, S1a obtained as bottoms stream contains at most 100 weight-ppm, preferably at most 50 weight-ppm, more preferably at most 10 weight-ppm of the propylene oxide, based on the total weight of S1a.

Generally, the stream S1a as described above can be used as acetonitrile recycle stream which can be used for providing the liquid feed stream in (a) (described herein later below). Further, it is possible that the stream S1a is subjected to further work-up steps before it is used as acetonitrile recycle stream which is used for providing the liquid feed stream in (a). Preferably, a part of S1a is introduced to the distillation unit employed for the separation in (d) (described herein later below) as extracting agent, preferably in the upper part of the distillation unit.

Stream S1c

According to (ii.1), a gaseous top stream S1c is obtained from the first distillation unit, which is enriched in propylene oxide compared to the stream S0. Preferably, the top stream S1c obtained in (ii.1) contains at least 99.00 weight-%, more preferably at least 99.50 weight-%, more preferably at least 99.80 weight-%, propylene oxide based on the total weight of S1c. Preferably, the top stream S1c obtained in (ii.1) contains at the outmost 0.2 weight-%, more preferably at the outmost 0.18 weight-%, more preferably at the outmost 0.15 weight-% of the organic compound comprising a carbonyl group based on the total weight of Sic, more preferably at the outmost 15 weight-ppm propionaldehyde and at the outmost 5 weight-ppm acetone based on the total weight of Sic.

Further preferably, the top stream S1c obtained in (ii.1) contains at the outmost 100 weight-ppm, preferably at the outmost 75 weight-ppm, more preferably at the outmost 50 weight-ppm water based on the total weight of S1c.

Preferably, the process for purifying propylene oxide according to the present invention is a continuous process.

Origin of Stream S0

Generally, no restrictions exist from where the stream S0 originates and it can be provided in (i) according to any conceivable method. In one preferred embodiment of the present invention, the stream S0 is obtainable or obtained by a, preferably continuous, process comprising (a) providing a stream comprising propene and preferably propane, hydrogen peroxide, water, and acetonitrile;

(b) passing the liquid feed stream provided in (a) into an epoxidation zone comprising an epoxidation catalyst comprising a titanium zeolite, and subjecting the liquid feed stream to epoxidation reaction conditions in the epoxidation zone, obtaining a reaction mixture comprising propene and preferably propane, propylene oxide, water, acetonitrile, and the organic compound comprising a carbonyl group;

(c) removing an effluent stream from the epoxidation zone, the effluent stream comprising propylene oxide, water, acetonitrile, propene and preferably propane, and the organic compound comprising a carbonyl group;

(d) separating propene and preferably propane from the effluent stream by distillation, comprising subjecting the effluent stream to distillation conditions in a distillation unit, obtaining a gaseous stream which is enriched in propene and preferably propane compared to the effluent stream subjected to distillation conditions, and a liquid bottoms stream which is enriched in propylene oxide, water, acetonitrile and the organic compound comprising a carbonyl group compared to the effluent stream subjected to distillation conditions;

wherein said liquid bottoms stream obtained according to (d) is the stream S0.

In another preferred embodiment of the present invention providing the stream S0 according to (i) comprises (a) providing a stream comprising propene and preferably propane, hydrogen peroxide, water, and acetonitrile;

(b) passing the liquid feed stream provided in (a) into an epoxidation zone comprising an epoxidation catalyst comprising a titanium zeolite, and subjecting the liquid feed stream to epoxidation reaction conditions in the epoxidation zone, obtaining a reaction mixture comprising propene and preferably propane, propylene oxide, water, acetonitrile, and the organic compound comprising a carbonyl group;

(c) removing an effluent stream from the epoxidation zone, the effluent stream comprising propylene oxide, water, acetonitrile, propene and preferably propane, and the organic compound comprising a carbonyl group;

(d) separating propene and preferably propane from the effluent stream by distillation, comprising subjecting the effluent stream to distillation conditions in a distillation unit, obtaining a gaseous stream which is enriched in propene and preferably propane compared to the effluent stream subjected to distillation conditions, and a liquid bottoms stream which is enriched in propylene oxide, water, acetonitrile and and the organic compound comprising a carbonyl group compared to the effluent stream subjected to distillation conditions; wherein said liquid bottoms stream obtained according to
(d) is the stream S0. The steps (a) to (d) are preferably done in a continuous manner.

Preferably, the effluent stream removed according to (c) further comprises oxygen, wherein (d) comprises separating oxygen, propene and preferably propane from the effluent stream by distillation, comprising subjecting the effluent stream to distillation conditions in a distillation unit, obtaining a gaseous stream which is enriched in oxygen, propene and preferably propane compared to the effluent stream subjected to distillation conditions, and a liquid bottoms stream which is enriched in propylene oxide, water and acetonitrile compared to the effluent stream subjected to distillation conditions.

Preferably, the effluent stream removed according to (c) is depressurized prior to (d), preferably to a pressure of from 0.5 to 2.8 bar, more preferably of from 0.6 to 2.5 bar, more preferably of from 0.8 to 1.5 bar. More preferably, a gaseous stream and a liquid stream are obtained from depressurizing the effluent stream, wherein more preferably the gaseous and liquid streams are passed separately to the distillation unit, preferably the distillation tower, employed according to (d), more preferably to different theoretical trays of the distillation tower employed according to (d).

Generally, the stream comprising propene and preferably propane, hydrogen peroxide, water, and acetonitrile can be provided in (a) according to any conceivable method. Preferably, the stream is provided in (a) by combining at least three individual streams wherein a first stream comprises hydrogen peroxide, a second stream comprises propene and preferably propane and a third stream comprises acetonitrile and optionally water.

Preferably, the stream comprising propene additionally comprises propane wherein preferably at least 98 weight-%, more preferably at least 99 weight-%, more preferably at least 99.5 weight-%, more preferably at least 99.9 weight-% of the stream consist of propene and propane. Preferably, the weight ratio of propene relative to propane in the stream is at least 7:3. For example, commercially available propene can be employed which may be either a polymer grade propene or a chemical grade propene. Typically, polymer grade propene has a propene content in the range of from 99 to 99.8 weight-% and a propane content in the range of from 0.2 to 1 weight-%. Chemical grade propene typically has a propene content in the range of from 92 to 98 weight-% and a propane content in the range of from 2 to 8 weight-%. Preferably, a stream is employed having a propene content in the range of from 99 to 99.8 weight-% and a propane content in the range of from 0.2 to 1 weight-%.

The stream comprising hydrogen peroxide can be prepared according to every conceivable method. It is conceivable to obtain the stream comprising hydrogen peroxide by converting sulphuric acid into peroxodisulphuric acid by anodic oxidation with simultaneous evolution of hydrogen at the cathode. Hydrolysis of the peroxodisulphuric acid then leads via peroxomonosulphuric acid to hydrogen peroxide and sulphuric acid which is thus obtained back. The preparation of hydrogen peroxide from the elements is also conceivable. Depending on the specific preparation method, the stream comprising hydrogen peroxide can be, for example, an aqueous or an aqueous/methanolic hydrogen peroxide stream, preferably an aqueous hydrogen peroxide stream. In case an aqueous hydrogen peroxide feed is employed, the content of the stream with respect to hydrogen peroxide is usually in the range of from 3 to 85 weight-%, preferably from 25 to 75 weight-%, more preferably from 30 to 50 weight-%, such as from 30 to 40 weight-% or from 35 to 45 weight-% of from 40 to 50 weight-%. Preferably, at least 25 weight-%, more preferably at least 30 weight-%, more preferably at least 35 weight-% of the stream comprising hydrogen peroxide consist of water and hydrogen peroxide. Preferred ranges are from 30 to 80 weight % or from 35 to 75 weight-% or from 40 to 70 weight-%.

According to the present invention, it is preferred to employ a stream comprising hydrogen peroxide which is obtained as crude hydrogen peroxide solution by extraction of a mixture which results from a process known as anthraquinone process by means of which virtually the entire world production of hydrogen peroxide is produced (see, e.g., Ullmann's Encyclopedia of Industrial Chemistry, $5^{th}$ edition, volume A 13 (1989) pages 443-466) wherein a solution of an anthraquinone is used containing an alkyl group preferably having of from 2 to 10 carbon atoms, more preferably at least 5 carbon atoms such as 5 carbon atoms or 6 carbon atoms and where the solvent used usually consists of a mixture of two different solvents, wherein preferably none of the solvents is a nitrogen containing substance. This solution of the anthraquinone is usually referred to as the working solution. In this process, the hydrogen peroxide formed in the course of the anthraquinone process is generally separated by extraction from the respective working solution after a hydrogenation/re-oxidation cycle. Said extraction can be performed preferably with essentially pure water, and the crude aqueous hydrogen peroxide solution is obtained. While it is generally possible to further purify the thus obtained crude aqueous hydrogen peroxide solution by distillation, it is preferred, according to the present invention, to use such crude aqueous hydrogen peroxide solution which has not been subjected to purification by distillation. Further, it is generally possible to subject the crude aqueous hydrogen peroxide solution to a further extraction stage wherein a suitable extracting agent, preferably an organic solvent is used. More preferably, the organic solvent used for this further extraction stage is the same solvent which is used in the anthraquinone process. Preferably the extraction is performed using just one of the solvents in the working solution and most preferably using just the most nonpolar solvent of the working solution. In case the crude aqueous hydrogen peroxide solution is subjected to such further extraction stage, a so-called crude washed hydrogen peroxide solution is obtained. According to a preferred embodiment of the present invention, the crude washed hydrogen peroxide solution is used as hydrogen peroxide feed. The production of a crude solution is described, for example, in European patent application EP 1 122 249 A1. As to the term "essentially pure water", reference is made to paragraph 10, page 3 of EP 1 122 249 A1 which is incorporated by reference. The hydrogen peroxide can also be treated to remove trace metals, for example, as described in the WO 2015/049327 A1 before use.

It is conceivable that the hydrogen peroxide is prepared in situ in the epoxidation zone from hydrogen and oxygen, preferably in the presence of a suitable noble metal catalyst comprised in the epoxidation zone according to (b). A suitable noble metal catalyst preferably comprises one or more of palladium, platinum, silver, gold, rhodium, iridium, ruthenium and osmium. Preferably, the noble metal catalyst comprises palladium. The noble metal catalyst is preferably supported on a carrier, wherein the carrier preferably comprises one or more of $SiO_2$, $Al_2O_3$, $B_2O_3$, $GeO_2$, $Ga_2O_3$, $ZrO_2$, $TiO_2$, MgO, carbon and one or more zeolites, preferably one or more titanium zeolites. More preferably, the carrier comprises the epoxidation catalyst comprising a titanium zeolite. If hydrogen peroxide is prepared in the epoxidation zone according to (b) in situ from hydrogen and oxygen, the stream provided in (a) comprises propene and preferably propane, hydrogen, oxygen, water, and acetonitrile.

According to (b), the liquid feed stream provided in (a) is passed into an epoxidation zone. Generally, there are no specific restrictions regarding the design of the epoxidation zone provided that it is suitable for carrying out a, preferably continuous, epoxidation reaction. Preferably, the epoxidation zone according to (b) comprises one or more epoxidation subzone wherein a given epoxidation subzone preferably consist of one or more epoxidation reactors wherein, with regard to the design of the one or more epoxidation reactors, no specific restrictions exist provided that the reactors are suitable for carrying out a, preferably continuous, epoxidation reaction.

Preferably, the epoxidation zone according to (b) comprises a first epoxidation subzone consisting of one or more epoxidation reactors A. The term "first epoxidation subzone" as used in this context of the present invention relates to the epoxidation subzone into which the liquid feed stream provided in (a) is passed, wherein the epoxidation zone of (b) may comprise further epoxidation subzones which are arranged downstream of the first epoxidation subzone. If the first epoxidation subzone consisting of two or more epoxidation reactors A, it is preferred that the two or more epoxidation reactors A are arranged in parallel. In this case, it is preferred that in (b), the liquid feed stream provided in (a) is passed into at least one of the epoxidation reactors A. It is possible, for example, that, while the liquid feed stream provided in (a) is passed into at least one of the epoxidation reactors A, at least one of the reactors A is taken out of operation, for example for maintenance purposes and/or for regenerating the catalyst comprised in the at least one of the reactors A. If the first epoxidation subzone comprises two or more epoxidation reactors A, the reactors in operation are operated essentially identically so that in every epoxidation reactor A in operation, a given epoxidation condition is in the same range in every reactor.

The epoxidation conditions according to (b) comprise an epoxidation temperature TN, wherein TN is the temperature of a heat transfer medium used for adjusting the temperature of the reaction mixture in the first epoxidation reaction subzone according to (b) wherein it is preferred that said temperature is adjusted by passing the heat transfer medium through a jacket of the one or more epoxidation reactors A, wherein TN is preferably the temperature of the heat transfer medium prior to adjusting the temperature of the reaction mixture, preferably the temperature of the heat transfer medium at the entrance of the jacket of the one or more epoxidation reactors A. If the first epoxidation subzone comprises two or more epoxidation reactors A, the epoxidation temperature TN relates to the epoxidation temperature TN of a given reactor A in operation of first epoxidation subzone.

Preferably, the epoxidation conditions according to (b) comprise a first epoxidation reaction pressure in the range of from 14 to 100 bar, more preferably in the range of from 15 to 32 bar, more preferably in the range of from 15 to 25 bar. The first epoxidation reaction pressure is defined as the absolute pressure at the exit of the first epoxidation subzone. If the first epoxidation subzone comprises two or more epoxidation reactors A, the first epoxidation reaction pressure relates to the absolute pressures at the exit of a given reactor A in operation of first epoxidation subzone.

According to a first preferred embodiment of the present invention, the epoxidation zone according to (b) consists the first epoxidation subzone.

According to a second preferred embodiment of the present invention, the epoxidation zone according to (b) additionally comprises a second epoxidation subzone consisting of one or more epoxidation reactors B wherein, if the second epoxidation subzone comprises two or more epoxidation reactors B, the two or more epoxidation reactors B are arranged in parallel, wherein the second epoxidation subzone is arranged downstream of the first epoxidation subzone. In this case, it is preferred that in (b), the effluent stream obtained from the first epoxidation subzone, optionally after a suitable intermediate treatment, is passed into at least one of the epoxidation reactors B. It is possible, for example, that, while the effluent stream obtained from the first epoxidation subzone, optionally after a suitable intermediate treatment, is passed into at least one of the epoxidation reactors B, at least one of the reactors B is taken out of operation, for example for maintenance purposes and/or for regenerating the catalyst comprised in the at least one of the reactors B. If the second epoxidation subzone comprises two or more epoxidation reactors B, the reactors in operation are operated essentially identically so that in every epoxidation reactor B in operation, a given epoxidation condition is in the same range in every reactor. Generally, it is conceivable that in addition to the first epoxidation subzone and the second epoxidation subzone, the epoxidation zone according to (b) comprises at least one further epoxidation subzone arranged downstream of the second epoxidation subzone. Preferably, according to the second preferred embodiment of the present invention, the epoxidation zone according to (b) consists of the first epoxidation subzone and the second epoxidation subzone.

Preferably, the epoxidation conditions according to (b) comprise a second epoxidation reaction pressure in the range of from 14 to 100 bar, preferably in the range of from 14.5 to 32 bar, more preferably in the range of from 15 to 25 bar. The second epoxidation reaction pressure is defined as the absolute pressure at the exit of the second epoxidation subzone. If the second epoxidation subzone comprises two or more epoxidation reactors B, the second epoxidation reaction pressure relates to the absolute pressures at the exit of a given reactor B in operation of second epoxidation subzone.

Preferably, the epoxidation conditions according to (b) comprise an epoxidation catalyst loading in the second epoxidation subzone in the range of from 0.001 to 0.5 $h^{-1}$, more preferably in the range of from 0.005 to 0.3 $h^{-1}$, more preferably in the range of from 0.01 to 0.2 $h^{-1}$, wherein the epoxidation catalyst loading is defined as the ratio of the mass flow rate in kg/h of hydrogen peroxide contained in the feed stream passed into the second epoxidation subzone relative to the amount in kg of epoxidation catalyst comprising a titanium zeolite comprised in the second epoxidation subzone according to (b).

Preferably, the temperature of the reaction mixture in the second epoxidation reaction subzone is not adjusted by passing a heat transfer medium through a jacket of the one or more epoxidation reactors B. More preferably, the second epoxidation subzone is an essentially adiabatic epoxidation subzone. More preferably, the second epoxidation subzone is an adiabatic epoxidation subzone.

According to (b), the liquid feed stream provided in (a) is passed into an epoxidation zone comprising an epoxidation catalyst comprising a titanium zeolite. Preferably, the titanium zeolite comprised in the epoxidation catalyst is a titanium zeolite having ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAN, CAS, CDO, CFI, CGF, CGS, CHA, CHI, CLO, CON, CZP, DAC, DDR, DFO, DFT, DOH, DON, EAB, EDI, EMT, EPI, ERI, ESV, ETR, EUO, FAU, FER, FRA, GIS, GIU, GME, GON, GOO, HEU, IFR, ISV, ITE, ITH, ITW, IWR, IWW, JBW, KFI, LAU, LEV, LIO, LOS, LOV, LTA, LTL, LTN, MAR, MAZ, MEI, MEL, MEP, MER, MMFI, MFS, MON, MOR, MSO, MTF, MTN, MTT, MTW, MWW, NAB, NAT, NEES, NON, NPO, OBW, OFF, OSI, OSO, PAR, PAU, PHI, PON, RHO, RON, RRO, RSN, RTE, RTH, RUT, RWR, RWY, SAO, SAS, SAT, SAV, SBE, SBS, SBT, SFE, SFF, SFG, SFH, SFN SFO, SGT, SOD, SSY, STF, STI, STT, TER, THO, TON, TSC, UEI, UFI, UOZ, USI, UTL, VET, VFI, VNI, VSV, WEI, WEN, YUG, ZON framework structure or a mixed structure of two or more of these framework structures, preferably a titanium zeolite having an MFI framework structure, an MEL framework structure, an MWW framework structure, an ITQ framework structure, a BEA framework structure, a MOR framework structure, or a mixed structure of two or more of these framework structures, preferably an MWW framework structure.

More preferably, the titanium zeolite, preferably the titanium zeolite having an MWW framework structure, comprises at least one of Al, B, Zr, V, Nb, Ta, Cr, Mo, W, Mn, Fe, Co, Ni, Zn, Ga, Ge, In, Sn, Pb, Pd, Pt, Au, preferably at least one of B, Zr, V, Nb, Ta, Cr, Mo, W, Mn, Fe, Co, Ni, Zn, Ga, Ge, In, Sn, Pb, Pd, Pt, Au, more preferably Zn.

In one preferred embodiment, the titanium zeolite is an aluminum-free zeolitic material of MWW framework structure, containing titanium, preferably in an amount of from 0.5 to 5 weight-%, more preferably from 1 to 2 weight-%, calculated as elemental titanium and based on the total weight of the titanium containing zeolite, and containing zinc, preferably in an amount of from 0.5 to 5 weight-%, preferably from 1 to 2 weight-%, calculated as elemental zinc and based on the total weight of the titanium containing zeolite. The term "aluminum-free" in the context of the present invention refers to an embodiment according to which the aluminum content of the zeolitic material is 0.05 weight-ppm at most, preferably 0.03 weight-ppm at most, more preferably 0.02 weight-ppm at most, based on the total weight of the fresh, i.e. unused, zeolitic material. The weight-%-values refer to an embodiment according to which the zeolitic material is in dry state, preferably after drying for at least ten hours at 80° C. at a pressure of less than 1013.25 hPa.

The epoxidation catalyst comprising a titanium zeolite can be employed in every conceivable, including a powder, a micropowder, preferably a spray-powder, as a molding comprising a powder, or as a molding comprising a micropowder, preferably a spray-powder. Preferably, the catalyst comprising the titanium zeolite is employed as a molding comprising a powder or a micropowder, preferably a spray-powder, more preferably as a molding comprising a micropowder, preferably a spray-powder. More preferably, the catalyst comprising the titanium zeolite is present in the epoxidation zone as a molding, preferably as fluidized-bed catalyst or a fixed-bed catalyst, more preferably as a fixed-bed catalyst.

The process is preferably a continuous process.

The present invention is further illustrated by the following set of embodiments and combinations of embodiments resulting from the given dependencies and back-references.

1. A process for purifying propylene oxide, comprising
   (i) providing a stream S0 comprising propylene oxide, acetonitrile, water, and an organic compound comprising a carbonyl group —C(=O)—, wherein said organic compound comprising a carbonyl group —C(=O)— comprises one or more of acetone and propionaldehyde;
   (ii) separating propylene oxide from the stream S0 by distillation, comprising
      (ii.1) subjecting the stream S0 to distillation conditions in a first distillation unit, obtaining a gaseous top stream S1c which is enriched in propylene oxide compared to the stream S0, a liquid bottoms stream S1a which is enriched in acetonitrile and water compared to the stream S0, and a side stream S1b comprising propylene oxide which is enriched in the carbonyl compound compared to the stream S0;
      (ii.2) reacting the carbonyl compound comprised in the side stream S1b with an organic compound comprising an amino group —NH$_2$ obtaining a reaction product of the organic compound comprising a carbonyl group and the organic compound comprising an amino group;
      (ii.3) separating propylene oxide from the reaction product of the organic compound comprising a carbonyl group and the organic compound comprising an amino group in a second distillation unit, obtaining a gaseous top stream S3a which is enriched in propylene oxide and a liquid bottoms stream S3b which is enriched in the reaction product of the organic compound comprising a carbonyl group and the organic compound comprising an amino group;
      (ii.4) introducing the top stream S3a which is enriched in propylene oxide propylene oxide into the first distillation unit.
2. The process of embodiment 1, comprising
   (i) providing a stream S0 comprising propylene oxide, acetonitrile, water, and an organic compound comprising a carbonyl group —C(=O)—, wherein said organic compound comprising a carbonyl group —C(=O)— comprises one or more of acetone and propionaldehyde;
   (ii) separating propylene oxide from the stream S0 by distillation, comprising
      (ii.1) subjecting the stream S0 to distillation conditions in a first distillation unit, obtaining a gaseous top stream S1c which is enriched in propylene oxide compared to the stream S0, a liquid bottoms stream S1a which is enriched in acetonitrile and water compared to the stream S0, and a side stream S1b comprising propylene oxide which is enriched in the carbonyl compound compared to the stream S0;
      (ii.2) admixing the side stream S1b with an organic compound comprising an amino group —NH$_2$ and reacting the organic compound comprising a carbonyl group with the organic compound comprising an amino group, obtaining a stream S2 comprising propylene oxide and a reaction product of the organic compound comprising a carbonyl group and the organic compound comprising an amino group;

(ii.3) subjecting the stream S2 to distillation conditions in a second distillation unit, obtaining a gaseous top stream S3a which is enriched in propylene oxide compared to the stream S2, and a liquid bottoms stream S3b which is enriched in the reaction product of the organic compound comprising a carbonyl group and the organic compound comprising an amino group compared to the stream S2;

(ii.4) introducing the stream S3a into the first distillation unit.

3. The process of embodiment 1, comprising
   (i) providing a stream S0 comprising propylene oxide, acetonitrile, water, and an organic compound comprising a carbonyl group —C(=O)—, wherein said organic compound comprising a carbonyl group —C(=O)— comprises one or more of acetone and propionaldehyde;
   (ii) separating propylene oxide from the stream S0 by distillation, comprising
      (ii.1) subjecting the stream S0 to distillation conditions in a first distillation unit, obtaining a gaseous top stream S1c which is enriched in propylene oxide compared to the stream S0, a liquid bottoms stream S1a which is enriched in acetonitrile and water compared to the stream S0, and a side stream S1b comprising propylene oxide which is enriched in the carbonyl compound compared to the stream S0;
      (ii.2) subjecting the side stream S1b to distillation conditions in a second distillation unit and adding an organic compound comprising an amino group —NH$_2$ to the second distillation unit, preferably at the top of the second distillation unit, and reacting the organic compound comprising a carbonyl group with the organic compound comprising an amino group, obtaining a reaction product of the organic compound comprising a carbonyl group and the organic compound comprising an amino group, and obtaining a gaseous top stream S3a which is enriched in propylene oxide compared to the stream S1b, and a liquid bottoms stream S3b which is enriched in the reaction product of the organic compound comprising a carbonyl group and the organic compound comprising an amino group compared to the stream S1b;
      (ii.3) introducing the stream S3a into the first distillation unit.

4. The process of any one of embodiments 1 to 3, wherein the organic compound comprising a carbonyl group —C(=O)— comprised in the stream S0 further comprises one or more of acetaldehyde, formaldehyde, butyraldehyde, isobutyraldehyde, 2-butanon, 1-pentanal, 2-pentanon, 3-pentanon, 2-methylpentanone, preferably one ore more of acetaldehyde, formaldehyde, butyraldehyde, isobutyraldehyde, more preferably at least acetaldehyde.

5. The process of any one of embodiments 1 to 4, wherein the side stream S1b obtained in (ii.1) comprising propylene oxide and being enriched in the carbonyl compound compared to the stream S0 is further enriched in one or more of acetaldehyde, formaldehyde, butyraldehyde, isobutyraldehyde, 2-butanon, 1-pentanal, 2-pentanon, 3-pentanon, 2-methylpentanone, preferably one ore more of acetaldehyde, formaldehyde, butyraldehyde, isobutyraldehyde, more preferably at least in acetaldehyde.

6. The process any one of embodiments 1 to 5, wherein at least 95 weight-%, preferably at least 98 weight-%, more preferably at least 99 weight-% of the stream S0 consist of propylene oxide, acetonitrile, water, and the organic compound comprising a carbonyl group.

7. The process of any one of embodiments 1 to 6, wherein the stream S0 comprises the propylene oxide in amount of from 8 to 18 weight-%, preferably from 9 to 14 weight-%, based on the total weight of the stream S0; the acetonitrile in an amount of from 60 to 75 weight-%, preferably from 65 to 70 weight-%, based on the total weight of the stream S0; the water in amount of from 10 to 25 weight-%, preferably from 17 to 21 weight-%, based on the total weight of the stream S0; propionaldehyde in an amount of from 10 to 1000 weight-ppm, preferably from 30 to 500 weight-ppm, based on the total weight of the stream S0; acetone in an amount of from 50 to 400 weight-ppm, preferably from 60 to 120 weight-ppm, based on the total weight of the stream S0; and acetaldehyde in an amount of from 80 to 300 weight-ppm, preferably from 100 to 200 weight-ppm, based on the total weight of the stream S0.

8. The process of any one of embodiments 1 to 7, wherein the stream S0 is obtainable or obtained by a process comprising
   (a) providing a stream comprising propene and preferably propane, hydrogen peroxide, water, and acetonitrile;
   (b) passing the liquid feed stream provided in (a) into an epoxidation zone comprising an epoxidation catalyst comprising a titanium zeolite, and subjecting the liquid feed stream to epoxidation reaction conditions in the epoxidation zone, obtaining a reaction mixture comprising propene and preferably propane, propylene oxide, water, acetonitrile, and the organic compound comprising a carbonyl group;
   (c) removing an effluent stream from the epoxidation zone, the effluent stream comprising propylene oxide, water, acetonitrile, propene and preferably propane, and the organic compound comprising a carbonyl group;
   (d) separating propene and preferably propane from the effluent stream by distillation, comprising subjecting the effluent stream to distillation conditions in a distillation unit, obtaining a gaseous stream which is enriched in propene and preferably propane compared to the effluent stream subjected to distillation conditions, and a liquid bottoms stream which is enriched in propylene oxide, water, acetonitrile and and the organic compound comprising a carbonyl group compared to the effluent stream subjected to distillation conditions;
   wherein said liquid bottoms stream obtained according to (d) is the stream S0.

9. The process of any one of embodiments 1 to 7, wherein providing the stream S0 according to (i) comprises
   (a) providing a stream comprising propene and preferably propane, hydrogen peroxide, water, and acetonitrile;
   (b) passing the liquid feed stream provided in (a) into an epoxidation zone comprising an epoxidation catalyst comprising a titanium zeolite, and subjecting the liquid feed stream to epoxidation reaction conditions in the epoxidation zone, obtaining a reaction mixture comprising propene and preferably propane, propylene oxide, water, acetonitrile, and the organic compound comprising a carbonyl group;
   (c) removing an effluent stream from the epoxidation zone, the effluent stream comprising propylene oxide, water, acetonitrile, propene and preferably propane, and the organic compound comprising a carbonyl group;
   (d) separating propene and preferably propane from the effluent stream by distillation, comprising subjecting the effluent stream to distillation conditions in a distillation unit, obtaining a gaseous stream which is enriched in propene and preferably propane compared to the effluent stream subjected to distillation conditions, and a liquid bottoms stream which is enriched in propylene oxide, water, acetonitrile and and the organic compound comprising a carbonyl group compared to the effluent stream subjected to distillation conditions; wherein said liquid bottoms stream obtained according to (d) is the stream S0.

10. The process of embodiment 8 or 9, wherein the effluent stream removed according to (c) further comprises oxygen, wherein (d) comprises separating oxygen, propene and preferably propane from the effluent stream by distillation, comprising subjecting the effluent stream to distillation conditions in a distillation unit, obtaining a gaseous stream which is enriched in oxygen, propene and preferably propane compared to the effluent stream subjected to distillation conditions, and a liquid bottoms stream which is enriched in propylene oxide, water and acetonitrile compared to the effluent stream subjected to distillation conditions.

11. The process of any one of embodiments 8 to 10, wherein prior to (d), the effluent stream removed according to (c) is depressurized.

12. The process of embodiment 11, wherein from depressurizing the effluent stream, a gaseous stream and a liquid stream are obtained and wherein preferably the gaseous and liquid streams are passed separately to the distillation unit, preferably the distillation tower, employed according to (d), more preferably to different theoretical trays of the distillation tower employed according to (d).

13. The process of any one of embodiments 1 to 12, wherein the first distillation unit employed in (ii.1) is at least one distillation tower, preferably one distillation tower, wherein the distillation tower has preferably from 40 to 200, more preferably from 45 to 100, more preferably from 50 to 90, theoretical trays.

14. The process of any one of embodiments 1 to 13, wherein the rectifying section of the first distillation unit employed in (ii.1) consists of from 40 to 60% of the theoretical trays and the stripping section of the distillation unit consists of from 60 to 40% of the theoretical trays.

15. The process of any one of embodiments 1 to 14, wherein the first distillation unit employed in (ii.1) is operated at a top pressure of from 0.1 to 2.0 bar, preferably of from 0.2 to 1.0 bar, more preferably of from 0.3 to 0.8 bar.

16. The process of any one of embodiments 1 to 15, wherein the first distillation unit employed in (ii.1) is operated at a top temperature in the range of from 50 to 70° C., preferably of from 52 to 68° C., more preferably of from 54 to 64° C.

17. The process of any one of embodiments 1 to 16, wherein the first distillation unit employed in (ii.1) is operated at an internal reflux ratio in the range of from 1 to 10, preferably from 2 to 8, more preferably from 3 to 6.

18. The process of any one of embodiments 1 to 17, wherein the side stream S1b obtained in (ii.1) is removed from the rectifying section of the first distillation unit.

19. The process of any one of embodiments 1 to 18, wherein the side stream S1b obtained in (ii.1) is removed from the rectifying section of the first distillation unit at a position which is at least 1 theoretical tray above the stripping section of the first distillation unit.

20. The process of any one of embodiments 1 to 19, wherein the side stream S1b obtained in (ii.1) is removed from the rectifying section of the first distillation unit at a position which is from 1 to 15, preferably from 1 to 12, more preferably from 1 to 10, theoretical tray above the stripping section of the first distillation unit.

21. The process of any one of embodiments 1 to 20, wherein at least 95 weight-%, preferably at least 98 weight-%, more preferably at least 99 weight-% of the stream S1b consist of propylene oxide, acetonitrile, water, and the organic compound comprising a carbonyl group.

22. The process of any one of embodiments 1 to 21, wherein the stream S1b comprises the propylene oxide in an amount of from 68 to 96 weight-%, preferably from 70 to 95 weight-%, based on the total weight of the stream S1b; the acetonitrile in an amount of from 2 to 25 weight-%, preferably from 3.5 to 22 weight-%, based on the total weight of the stream S1b; the organic compound comprising a carbonyl group in an amount of from 0.05 to 4 weight-%, preferably from 0.1 to 2.6 weight-%; based on the total weight of the stream S1b; wherein the organic compound comprising a carbonyl group preferably comprises propionaldehyde in an amount of from 0.03 to 3 weight-%, preferably from 0.05 to 2.0 weight-%, based on the total weight of the stream Sib, and acetone in an amount of from 0.01 to 1.0 weight-%, preferably from 0.02 to 0.6 weight-%, based on the total weight of the stream S1b, and acealdehyde in an amount of from 0.01 to 0.5 weight-%, preferably from 0.03 to 0.1 weight-%, based on the total weight of the stream Sib.

23. The process of any one of embodiments 1 to 22, wherein the organic compound comprising an amino group —NH$_2$ comprises one or more of R—NH$_2$, wherein R is a substituted or unsubstituted, branched or unbranched C1-C5-alkyl, preferably selected from the group consisting of ethyl amine, n-propyl amine, iso-propyl amine, n-butyl amine, iso-butyl amine, ethanol amine; R1-NH$_2$, wherein R1 is a C6-C10-aryl group with at least one further substituent R2 selected from the group consisting of hydrogen, —CH$_3$, —NO$_2$ positioned at the aryl group, preferably selected from the group consisting of aniline, toluidine, ortho-nitroaniline, alpha-naphthylamine, beta-naphthylamine; NH$_2$—R3-NH$_2$, wherein R3 is selected from the group consisting of C2-C3-alkylene groups or phenyl, preferably selected from the group consisting of 1,2-diamino ethane, 1,2-diamino propane, 1,3-diamino propane, 1,2-diamino benzene, 1,3-diamino benzene, 1,4-diamino benzene; N—C1-C6-aminales; carbonic acid amides, preferably selected from the group consisting of acetamide, propanamide, iso-butyramide, benzene sulfonamide, para-toluenesulfonamide; amide of the monomethylester of methylphosphonic acid; amides of carbonic acids, preferably selected from the group consisting of urea, N—C1-C6-alkyl urea, N,N'—C1-C6-dialkyl urea; amino acids, preferably selected from the group consisting of glycine, alanine, norvaline, methionine, valine, lysine; anthranilic acid; nitriles of alpha-amino carbonic acids, preferably alpha-amino-propionitrile; cyanamide; hydroxylamine; O-methylhydroxylamine; hydroxylamine-O-sufonic acid; hydrazine; hydrazine monohydrate; monoC1-C4-alkyl hydrazines, preferably selected from the group consisting of methyl hydrazine, ethyl hydrazine, propyl hydrazine, butyl hydrazine, iso-propyl hydrazine; aryl hydrazines, preferably selected from the group consisting of phenylhydrazine, 2,4-dinitrophenylhydrazine; dialkyl hydrazines, preferably N,N-dimethyl hydrazine; hydrazides, preferably selected from the group consisting of semi carbazide, acethydrazide, benzoic acid hydrazide, iso-butanoic acid hydrazide; and hydrazides of thiocarbonic acids of the formula R4(S═O)

2—NH—NH$_2$ wherein R4 is selected from the group consisting of C6-C10-aryl and C1-C6-alkyl; wherein the organic compound comprising an amino group —NH$_2$ preferably comprises hydrazine, more preferably hydrazine.
24. The process of any one of embodiments 1 to 23, wherein the organic compound comprising an amino group —NH$_2$ is used solid or dissolved, preferably dissolved in a solvent comprising water more preferably dissolvent in water.
25. The process of any one of embodiments 1 to 24, wherein the molar ratio of the molar amount of amino groups —NH$_2$ comprised in the organic compound comprising an amino group —NH$_2$ used or admixed in (ii.2) to the molar amount of carbonyl groups comprised in the organic compound comprising a carbonyl group is in the range of from 0.5:1 to 100:1, preferably from 0.75:1 to 25:1, more preferably from 1:1 to 10:1.
26. The process of any one of embodiments 2 or 4 to 25, wherein the reacting of the organic compound comprising a carbonyl group with the organic compound comprising an amino group —NH$_2$ in (ii.2) is done in one or more reactors, preferably in one reactor, more preferably in a tube reactor.
27. The process of any one of embodiments 2 or 4 to 26, wherein the residence time for reacting the organic compound comprising a carbonyl group with the organic compound comprising an amino group in (ii.2) is at least 0.1 h, preferably from 0.3 to 2.0 h.
28. The process of any one of embodiments 2 or 4 to 27, wherein the organic compound comprising a carbonyl group is reacted with the organic compound comprising an amino group in (ii.2) at a temperature in the range of from 10 to 80° C., preferably from 20 to 60° C.
29. The process of any one of embodiments 1 to 28, wherein the second distillation unit employed in (ii.3) is at least one distillation tower, preferably one distillation tower, wherein the distillation tower has preferably at least 5, more preferably from 5 to 25, more preferably from 8 to 20, theoretical trays.
30. The process of any one of embodiments 1 to 29, wherein the rectifying section of the second distillation unit employed in (ii.3) consists of from 90 to 100%, preferably from 95 to 100%, more preferably from 99 to 100%, of the theoretical trays.
31. The process of any one of embodiments 1 to 30, wherein the second distillation unit employed in (ii.3) is operated at a top pressure of from 0.1 to 2.0 bar, preferably of from 0.2 to 1.0 bar, more preferably of from 0.3 to 0.8 bar.
32. The process of any one of embodiments 1 to 31, wherein the first distillation unit employed in (ii.1) is operated at a bottoms temperature in the range of from 30 to 50° C., preferably of from 32 to 45° C., more preferably of from 36 to 40° C.
33. The process of any one of embodiments 1 to 32, wherein the gaseous top stream S3$a$ obtained in (ii.3) is introduced into the first distillation unit in (ii.4) in the rectifying section of the first distillation unit at a position which is at least 1 theoretical tray above the stripping section of the first distillation unit, preferably at a position which is from 1 to 15, preferably from 1 to 12, more preferably from 1 to 10, theoretical tray above the stripping section of the first distillation unit.
34. The process of any one of embodiments 1 to 33, wherein the gaseous top stream S3$a$ obtained in (ii.3) is introduced into the first distillation unit in (ii.4) in the rectifying section of the first distillation unit at a position which is 0 to 3 theoretical trays, preferably 0 theorectical trays above the theoretical tray where the side stream S1$b$ obtained in (ii.1) is removed from the rectifying section of the first distillation.
35. The process of any one of embodiments 1 to 34, wherein at least 95 weight-% of S1$a$ consist of acetonitrile and water, wherein preferably, the weight ratio of acetonitrile relative to water in the stream S1$a$ is greater than 1:1.
36. The process of any one of embodiments 1 to 35, wherein S1$a$ obtained as bottoms stream contains at most 100 weight-ppm, preferably at most 50 weight-ppm, more preferably at most 10 weight-ppm of the propylene oxide, based on the total weight of S1$a$.
37. The process of any one of embodiments 1 to 36, wherein a part of S1$a$ is introduced to the distillation unit employed for the separation in (d) according to any one of embodiments 7 to 9 as extracting agent, preferably in the upper part of the distillation unit.
38. The process of any one of embodiments 1 to 37, wherein the top stream S1$c$ obtained in (ii.1) contains at least 99.00 weight-%, more preferably at least 99.50 weight-%, more preferably at least 99.80 weight-%, propylene oxide based on the total weight of S1$c$.
39. The process of any one of embodiments 1 to 38, wherein the top stream S1$c$ obtained in (ii.1) contains at the outmost 0.2 weight-%, preferably at the outmost 0.18 weight-%, more preferably at the outmost 0.15 weight-% of the organic compound comprising a carbonyl group based on the total weight of S1$c$, more preferably at the outmost 15 weight-ppm propionaldehyde and at the outmost 5 weight-ppm acetone based on the total weight of S1$c$.
40. The process of any one of embodiments 1 to 39, wherein the top stream S1$c$ obtained in (ii.1) contains at the outmost 100 weight-ppm, preferably at the outmost 75 weight-ppm, more preferably at the outmost 50 weight-ppm water based on the total weight of S1$c$.
41. The process of any one of embodiments 1 to 40, which is a continuous process.

The present invention is further illustrated by the following reference examples, comparative examples, and examples.

EXAMPLES

Reference Example 1: Preparation of a Catalyst Comprising a Titanium Zeolite Having Framework Type MWW 1.1 Preparation of Boron Containing Zeolite of Structure MWW (BMWW)

A 2 m$^3$ stirred tank reactor was first loaded with 470.4 kg of deionized water. After starting the stirrer at 70 rpm, boric acid (162.5 kg) was added and the suspension was stirred for 3 h. Subsequently, piperidine (272.5 kg) was added at once causing the temperature to rise from 28° C. to 46° C. To this solution colloidal silica (Ludox® AS040, 392.0 kg) was added. The reactor was then slowly heated to 170° C. within 5 hours and then kept at this temperature under stirring for 120 hours. The maximum pressure during the reaction was 9.3 bar. Afterwards the reactor was cooled down to 50° C. The gel obtained had a pH of 11.3 and a viscosity of 15 mPa·s at 20° C. The gel was then filtered and the filter cake washed with deionized water until the conductivity of the washings was below 500 microSiemens/cm. The filter cake was then suspended in deionized water and the suspension was spray-dried at 235° C. using nitrogen as the carrier gas.

The white powder obtained (174.3 kg) contained 3.5 weight-% water. This white powder was then calcined at 650° C. in a rotary kiln to give 138.2 kg of boron containing zeolite of structure type MWW (BMWW) as a white powder.

1.2 Deboronation of BMWW with Water

A 5 m³ stirred tank reactor was loaded with 125 kg of the BMWW obtained according to the previous step 1.1 and 3750 kg of deionized water. The reactor was then slowly heated to 100° C. within 1 hour under stirring at 70 rpm, and then kept at this temperature for 20 hours and finally cooled to a temperature below 50° C. before it was filtered. The filter cake was then washed with deionized water until the washings had conductivity below 15 microSiemens/cm. The filter cake was then dried for 6 hours under a nitrogen stream. The filter cake was then removed and suspended in 850 kg of deionized water. This suspension was then spray-dried at 235° C. using nitrogen as the carrier gas. The spray dried material weighed 118.5 kg and contained 42.5 weight-% Si, 0.06 weight-% B and 0.23 weight-% C (total organic carbon, TOC).

1.3 Preparation of Titanium Containing Zeolite of Structure Type MWW (TiMWW)

A 2 m³ stirred tank reactor was first loaded with 111.2 kg of the spray-dried material from the previous step 1.2. In a separate 2 m³ stirred tank reactor were placed 400 kg of deionized water. After starting the stirrer at 80 rpm, piperidine (244.0 kg) was added. After the addition of piperidine was finished the mixture was stirred for 5 minutes before tetrabutyl orthotitanate (22.4 kg) was added. The pipe through which the titanate was added was then flushed with 40 kg of deionized water. The mixture was then stirred for 1 hour before being added to the first stirred tank reactor containing the spray-dried powder under stirring (50 rpm). The reactor was then heated to 170° C. and kept at this temperature for 120 h before being cooled to 50° C. The maximum pressure during the reaction was 10.6 bar. The cooled suspension was then filtered and the filter cake was washed with deionized water until the washings had conductivity below 1300 microSiemens/cm and an approximately neutral pH value. The filter cake was then dried under a nitrogen stream for 6 hours. The filter cake containing about 80 weight-% of water was used directly for the next step. The filter cake from the previous step and 1000 kg of deionized water were filled in a 2 m³ stirred tank reactor. Then 1900 kg of nitric acid (53 weight-% in water) were added under stirring at 70 rpm. The reactor was then heated to 100° C. and kept at this temperature for 20 hours before being cooled to 50° C. The suspension obtained was then filtered and the filter cake was washed with deionized water until the conductivity was below 10 microSiemens/cm and the washings were approximately neutral. Subsequently the filter cake was dried under a stream of nitrogen for 6 hours. This filter cake was then suspended in water and spray-dried at 235° C. using nitrogen as the carrier gas. 96 kg of a spray-dried powder were obtained. This material was then calcined in a rotary kiln at 650° C. 84 kg of titanium zeolite of structure type MWW (TiMWW) were obtained as a powder containing 43 weight-% Si, 2.0 weight-% Ti and 0.2 weight-% C (TOC). The pore volume determined by Hg-porosimetry according to DIN 66133 was 7.3 ml/g and the BET surface area determined according to DIN 66131 was 467 m²/g.

1.4 Preparation of a Zinc Containing TiMWW (ZnTiMWW) by Impregnation a) In a vessel equipped with a reflux condenser, a solution of 981 kg deionized water and 6.0 kg zinc acetate dihydrate was prepared within 30 min. Under stirring (40 r.p.m.), 32.7 kg of the calcined Ti-MWW material obtained according to 1.3 above were suspended. Subsequently, the vessel was closed and the reflux condenser put into operation. The stirring rate was increased to 70 r.p.m.

b) In a vessel equipped with a reflux condenser, a solution of 585 kg deionized water and 3.58 kg zinc acetate dihydrate was prepared within 30 min. Under stirring (40 r.p.m.), 19.5 kg of the calcined Ti-MWW material obtained according to 1.3 above were suspended. Subsequently, the vessel was closed and the reflux condenser put into operation. The stirring rate was increased to 70 r.p.m.

In all batches a) and b), the mixture in the vessel was heated to 100° C. within 1 h and kept under reflux for 2 h at a stirring rate of 70 r.p.m. Then, the mixture was cooled within 2 h to a temperature of less than 50° C. For each batch a) and b), the cooled suspension was subjected to filtration, and the mother liquor was transferred to waste water discharge. The filter cake was washed five times with deionized water under a nitrogen pressure of 2.5 bar. After the last washing step, the filter cake was dried in a nitrogen stream for 10 h. In total 297 kg of nitrogen dried filter cake were obtained. The thus dried Zn-impregnated TiMWW material (ZnTiMWW), had a Si content of 42 weight-%, a Ti content of 1.8 weight-%, a Zn content of 1.3 weight-.%. From 297 kg of the mixture of the filter cake obtained above, an aqueous suspension was prepared with deionized water, the suspension having a solid content of 15 weight-%. This suspension was subjected to spray-drying in a spray-tower with the following spray-drying conditions:

apparatus used: spray tower with one nozzle
operation mode: nitrogen straight
configuration: dehumidifier-filter-scrubber
dosage: flexible-tube pump VF 10 (supplier: Verder)
   nozzle with a diameter of 4 mm (supplier: Niro)
filter material: Nomex® needle-felt 10 m²

|  |  | Runtime/h | | | | |
| --- | --- | --- | --- | --- | --- | --- |
|  |  | 0.5 | 1.5 | 2.5 | 3.5 | 4.5 |
|  | Flow rate gas/(kg/h) | 550 | 550 | 550 | 550 | 550 |
| Temperature drying gas/ ° C. | spray tower (in) | 305 | 305 | 305 | 305 | 305 |
|  | spray tower (out) | 151 | 151 | 151 | 151 | 151 |
|  | Filter (in) | 140 | 137 | 130 | 127 | 126 |
|  | Scrubber (in) | 110 | 110 | 110 | 108 | 105 |
|  | Scrubber (out) | 14 | 14 | 15 | 15 | 15 |
| Differential pressure/ mbar | spray tower | 3.1 | 3 | 3 | 2.8 | 2.9 |
|  | Filter | 1.7 | 1.7 | 1.8 | 1.8 | 2.1 |
|  | Scrubber | 3.8 | 4.1 | 4.2 | 4.2 | 4.2 |
| Pressure/ mbar | spray tower | −103 | −1.2 | −0.9 | −0.9 | −1.1 |
| Nozzle gas | Flow rate kg/h | 23 | 23 | 23 | 23 | 23 |
|  | Temperature/° C. | r.t.*) | r.t.*) | r.t.*) | r.t.*) | r.t.*) |
|  | Pressure/bar | 2.5 | 2.5 | 2.5 | 2.5 | 2.5 |
| Spray-dried product | Temperature/° C. | r.t.*) | r.t.*) | r.t.*) | r.t.*) | r.t.*) |

*)room temperature

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening. The spray-dried material thus obtained had a Zn content of 1.4 weight-%, a Ti content of 1.7 weight-%, a Si content of 41 weight-%, and a TOC content of <0.5 weight-%. The spray-dried product was then subjected to calcination for 2 h at 650° C. under air in a rotary furnace, yielding 43.8 kg of calcined spray-dried ZnTiMWW. The calcined spray-dried material thus obtained had a Zn content of 1.3 weight-%, a Ti content of 1.8 weight-%, a Si content of 42.5 weight-%, and a C content of <0.1 weight-%. The bulk density of the calcined spray-dried ZnTiMWW was 90 g/l (gram/liter). The mesopores of the micropowder had an average pore diameter (4V/A) of 20.2 nm as determined by Hg porosimetry according to DIN 66133. The macropores of the micropowder had an average pore diameter (4V/A) of 67.6 nm as determined by Hg porosimetry according to DIN 66133. The micropores of the ZnTiMWW contained in the micropowder had an average pore diameter of 1.06 nm as determined by nitrogen adsorption according to DIN 66134 (Horward-Kawazoe method). The Dv10 value of the particles of the micropowder was 4.10 micrometers. The Dv50 value of the particles of the micropowder was 8.19 micrometers. The Dv90 value of the particles of the micropowder was 14.05 micrometers. The degree of crystallization determined via XRD was (77+/−10) %, the average crystallite size 35.0 nm+/−10%. It was found that the crystalline phase exhibits a pure MWW structure. No other crystalline titania phases such as anatase, rutile or brookite, or crystalline zinc silicate ($Zn_2SiO_4$) such as willemite could be detected.

1.5 Preparation of Moldings Containing ZnTiMWW and Silica Binder

Starting from the calcined spray-dried ZnTiMWW material obtained according to 1.4 above, a molding was prepared, dried, and calcined. Therefor, 12 batches were prepared, each starting from 3.5 kg of the calcined spray-dried ZnTiMWW material obtained above, 0.226 kg Walocel™ (Walocel MW 15000 GB, Wolff Cellulosics GmbH & Co. KG, Germany), 2.188 kg Ludox® AS-40 and 6.6 l deionized water, as follows:

3.5 kg ZnTiMWW and 0.226 kg Walocel were subjected to kneading in an edge mill for 5 min. Then, during further kneading, 2.188 kg Ludox were added continuously. After another 10 min, addition of 6 l of deionized water was started. After another 30 min, further 0.6 l of deionized water were added. After a total time of 50 min, the kneaded mass had become extrudable. Thereafter, the kneaded mass was subjected to extrusion under 65-80 bar wherein the extruder was cooled with water during the extrusion process. Per batch, the extrusion time was in the range of from 15 to 20 min. The power consumption per batch during extrusion was 2.4 A. A die head was employed allowing for producing cylindrical strands having a diameter of 1.7 mm. At the die head out outlet, the strands were not subjected to a cutting to length. The strands thus obtained were dried for 16 h at 120° C. in a drying chamber under air. In total (sum of the 12 batches), 56 kg white strands with a diameter of 1.7 mm were obtained. 56 kg of the dried strands were subjected to calcination in a rotary furnace at 550° C. for 1 h under air, yielding 52 kg calcined strands. Thereafter, the strands were sieved (mesh size 1.5 mm), and the yield, after sieving, was 50.0 kg. The thus obtained moldings exhibited a bulk density of 322 g/l (gram per liter) and had a Zn content of 1.1 weight-%, a Ti content of 1.4 weight-%, a Si content of 43 weight-%, and a C content of <0.1 weight-%. The mesopores of the micropowder had an average pore diameter (4V/A) of 20.9 nm as determined by Hg porosimetry according to DIN 66133. The macropores of the micropowder had an average pore diameter (4V/A) of 50.0 nm as determined by Hg porosimetry according to DIN 66133. The degree of crystallization determined via XRD was (70+/−10) %, the average crystallite size 32.5 nm+/−10%. The crush strength of the moldings as determined according to the method using a crush strength test machine Z2.5/TS01S was 4.4 N (standard deviation: 0.5 N). The minimum value found when testing the 10 samples was 3.5 N, the maximum value 5.1 N. In the $^{29}Si$ MAS NMR, after the curve had been deconvolved by the proper Gaussian-Lorentzian line shapes, six peaks were clearly observed. The $Q^3/Q^4$ ratio was found to be 2.2. The total amount of adsorbed water as determined according to Reference Example 6 of the molding was 6.9 weight-%. The Langmuir surface are determined via nitrogen adsorption at 77 K according to DIN 66133 was 518 $m^2/g$, the mulitpoint BET specific surface area determined via nitrogen adsorption at 77 K according to DIN 66133 was 373 $m^2/g$. The total intrusion volume determined according to Hg porosimetry according to DIN 66133 was 1.3 ml/g (milliliter/gram), the respective total pore area 100.2 $m^2/g$. It was found that the crystalline phase of the moldings exhibits a pure MWW structure. No other crystalline titania phases such as anatase, rutile or brookite, or crystalline zinc silicate ($Zn_2SiO_4$) such as willemite could be detected via XRD.

Starting from the calcined strands, a post-treatment stage was performed as follows: 1,000 kg deioinized water were filled in a vessel. Then, 50 kg of the calcined moldings were added. The vessel was closed (pressure-tight), and the obtained mixture was heated to a temperature of 145° C. within 1.5 h and kept at this temperature under autogenous pressure (about 3 bar) for 8 h. Then, the mixture was cooled for 2 h. The water-treated strands were subjected to filtration and washed with deionized water. The obtained strands were heated in a drying chamber under air within 1 h to a temperature of 120° C. and kept at this temperature for 16 h. Subsequently, the dried material was heated under air to a temperature of 450° C. within 5.5 h and kept at this temperature for 2 h. Thereafter, the strands were sieved (mesh size 1.5 mm), and the yield, after sieving, was 49.1 kg. The thus obtained water-treated moldings exhibited a bulk density of 332 g/l (gram per liter) and had a Zn content of 1.1 weight-%, a Ti content of 1.4 weight-%, a Si content of 42 weight-%, and a C content of <0.10 weight-%. The mesopores of the micropowder had an average pore diameter (4V/A) of 22.1 nm as determined by Hg porosimetry according to DIN 66133. The macropores of the micropowder had an average pore diameter (4V/A) of 52.0 nm as determined by Hg porosimetry according to DIN 66133. The degree of crystallization determined via XRD was (69+/−10) %, the average crystallite size 30.5 nm+/−10%. The crush strength of the moldings as determined according to the method using a crush strength test machine Z2.5/TS01S was 13.7 N (standard deviation: 2.5 N). The minimum value found when testing the 10 samples was 10.2 N, the maximum value 17.6 N. In the $^{29}Si$ MAS NMR, after the curve had been deconvolved by the proper Gaussian-Lorentzian line shapes, six peaks were clearly observed. The $Q^3/Q^4$ ratio was found to be 1.39. The total amount of adsorbed water of the molding was 6.9 weight-%. The intensity ratio of the infrared band in the region of (3746+/−20) $cm^{-1}$ attributed to the free silanol groups, relative to the infrared band in the region of 3688+/−20 $cm^{-1}$ attributed to vicinal silanol groups was smaller than 1.4. The Langmuir surface are determined via nitrogen adsorption at 77 K according to DIN 66133 was 421 $m^2/g$, the multipoint BET specific surface area determined via nitrogen adsorption at 77 K according t DIN 66133 was 303 m$^2$/g. The total intrusion volume determined according to Hg porosimetry according to DIN 66133 was 1.3 ml/g (milliliter/gram), the respective total pore area 98.7 m$^2$/g. It was found that the crystalline phase of the moldings exhibits a pure MWW structure. No other crystalline titania phases such as anatase, rutile or brookite, or crystalline zinc silicate ($Zn_2SiO_4$) such as willemite could be detected via XRD.

Reference Example 2: Characterization of the Catalyst

Reference Example 2.1: Determination of Dv10, Dv50, and Dv90 Values 1.0 g of the micropowder is suspended in 100 g deionized water and stirred for 1 min. The sample was subjected to the measurement in an apparatus using the following parameters: Mastersizer S long bed version 2.15, ser. No. 33544-325; supplier: Malvern Instruments GmbH, Herrenberg, Germany: focal width 300RF mm; beam length 10.00 mm; module MS017; shadowing 16.9%; dispersion model 3$$D; analysis model polydisperse correction none.

Reference Example 2.2: Determination of the Silanol Concentration of the Moldings of the Present Invention For the determination of the silanol concentration, the $^{29}$Si MAS NMR experiments were carried out at room temperature on a VARIAN Infinityplus-400 spectrometer using 5.0 mm $ZrO_2$ rotors. The $^{29}$Si MAS NMR spectra were collected at 79.5 MHz using a 1.9 μs Tr/4 (microsecond pi/4) pulse with 10 s recycle delay and 4000 scans. All $^{29}$Si spectra were recorded on samples spun at 6 kHz, and chemical shifts were referenced to 4,4-dimethyl-4-silapentane sulfonate sodium (DSS). For the determination of the silanol group concentration, a given $^{29}$Si MAS NMR spectrum is deconvolved by the proper Gaussian-Lorentzian line shapes. The concentration of the silanol groups with respect to the total number of Si atoms is obtained by integrating the deconvolved $^{29}$Si MAS NMR spectra.

Reference Example 2.3: Determination of the Crush Strength of the Moldings

The crush strength as referred to in the context of the present invention is to be understood as determined via a crush strength test machine Z2.5/TS01S, supplier Zwick GmbH & Co., D-89079 Ulm, Germany. As to fundamentals of this machine and its operation, reference is made to the respective instructions handbook "Register 1: Betriebsanleitung/Sicherheitshandbuch für die Material-Prüfmaschine Z2.5/TS01S", version 1.5, December 2001 by Zwick GmbH & Co. Technische Dokumentation, August-Nagel-Strasse 11, D-89079 Ulm, Germany. With said machine, a given strand is subjected to an increasing force via a plunger having a diameter of 3 mm until the strand is crushed. The force at which the strand crushes is referred to as the crushing strength of the strand. The machine is equipped with a fixed horizontal table on which the strand is positioned. A plunger which is freely movable in vertical direction actuates the strand against the fixed table. The apparatus was operated with a preliminary force of 0.5 N, a shear rate under preliminary force of 10 mm/min and a subsequent testing rate of 1.6 mm/min. The vertically movable plunger was connected to a load cell for force pick-up and, during the measurement, moved toward the fixed turntable on which the molding (strand) to be investigated is positioned, thus actuating the strand against the table. The plunger was applied to the stands perpendicularly to their longitudinal axis. Controlling the experiment was carried out by means of a computer which registered and evaluated the results of the measurements. The values obtained are the mean value of the measurements for 10 strands in each case.

Reference Example 2.4: $^{29}$Si Solid-State NMR Spectra Regarding $Q^3$ and $Q^4$ Structures The effect of the inventive water treatment on the molding related to $Q^3$ and $Q^4$ structures in the material was characterized by comparing the changes in $^{29}$Si solid-state NMR spectra under comparable conditions. All $^{29}$Si solid-state NMR experiments were performed using a Bruker Advance spectrometer with 300 MHz $^1$H Larmor frequency (Bruker Biospin, Germany). Samples were packed in 7 mm $ZrO_2$ rotors, and measured under 5 kHz Magic Angle Spinning at room temperature. $^{29}$Si direct polarization spectra were obtained using (pi/2)-pulse excitation with 5 microsecond pulse width, a $^{29}$Si carrier frequency corresponding to −65 ppm in the spectrum, and a scan recycle delay of 120 s. Signal was acquired for 25 ms under 45 kHz high-power proton decoupling, and accumulated over 10 to 17 hours. Spectra were processed using Bruker Topspin with 30 Hz exponential line broadening, manual phasing, and manual baseline correction over the full spectrum width. Spectra were referenced with the polymer Q8M8 as an external secondary standard, setting the resonance of the trimethylsilyl M group to 12.5 ppm. The spectra were then fitted with a set of Gaussian line shapes, according to the number of discernable resonances. Relating to the presently assessed spectra, 6 lines in total were used, accounting for the five distinct peak maxima (at approximately −118, −115, −113, −110 and −104 ppm) plus the clearly visible shoulder at −98 ppm. Fitting was performed using DMFit (Massiot et al., Magnetic Resonance in Chemistry, 40 (2002) pp 70-76). Peaks were manually set at the visible peak maxima or shoulder. Both peak position and line width were then left unrestrained, i.e., fit peaks were not fixed at a certain position. The fitting outcome was numerically stable, i.e., distortions in the initial fit setup as described above did lead to similar results. The fitted peak areas were further used normalized as done by DMFit. After the water treatment of the invention, a decrease of signal intensity at the left hand side of the spectrum was observed, a region that includes $Q^3$ silanol structures (here especially: around and above −104 ppm, i.e. "left" of −104 ppm). Further, an increase of signal at the right hand side of the spectrum (here: below −110 ppm, i.e. "right" of −110 ppm) was observed, which region comprises $Q^4$ structures exclusively. For the quantification of spectrum changes, a ratio was calculated that reflects changes in the peak areas "left hand" and "right hand", as follows. The six peaks were labeled with 1, 2, 3, 4, 5, and 6, and the ratio Q was calculated with the formula 100*{$[a_1+a_2]/[a_4+a_5+a_6]$}/$a_3$. In this formula, $a_{i, i=1 \ldots 6}$ represents the area of the fitted peak to which this number was attributed.

Reference Example 2.5: Water Adsorption/Desorption—Water Uptake

The water adsorption/desorption isotherms measurements were performed on a VTI SA instrument from TA Instruments following a step-isotherm program. The experiment consisted of a run or a series of runs performed on a sample material that has been placed on the microbalance pan inside of the instrument. Before the measurement were started, the residual moisture of the sample was removed by heating the sample to 100° C. (heating ramp of 5° C./min) and holding it for 6 h under a $N_2$ flow. After the drying program, the temperature in the cell was decreased to 25° C. and kept isothermal during the measurements. The microbalance was calibrated, and the weight of the dried sample was balanced (maximum mass deviation 0.01 weight-%). Water uptake by the sample was measured as the increase in weight over that of the dry sample. First, an adsorption curve was measured by increasing the relative humidity (RH) (expressed as weight-% water in the atmosphere inside of the cell) to which the samples was exposed and measuring the water uptake by the sample at equilibrium. The RH was increased with a step of 10 weight-% from 5 to 85% and at each step the system controlled the RH and monitored the sample weight until reaching the equilibrium conditions and recording the weight uptake. The total adsorbed water amount by the sample was taken after the sample was exposed to the 85 weight-% RH. During the desorption measurement the RH was decreased from 85 weight-% to 5 weight-% with a step of 10% and the change in the weight of the sample (water uptake) was monitored and recorded.

Reference Example 2.6: FT-IR Measurements

The FT-IR (Fourier-Transformed-Infrared) measurements were performed on a Nicolet 6700 spectrometer. The molding was powdered and then pressed into a self-supporting pellet without the use of any additives. The pellet was introduced into a high vacuum (HV) cell placed into the FT-IR instrument. Prior to the measurement the sample was pretreated in high vacuum ($10^{-5}$ mbar) for 3 h at 300° C. The spectra were collected after cooling the cell to 50° C. The spectra were recorded in the range of 4000 to 800 $cm^{-1}$ at a resolution of 2 $cm^{-1}$. The obtained spectra are represented in a plot having on the x axis the wavenumber ($cm^{-1}$) and on the y axis the absorbance (arbitrary units, a.u.). For the quantitative determination of the peak heights and the ratio between these peaks a baseline correction was carried out. Changes in the 3000-3900 $cm^{-1}$ region were analyzed and for comparing multiple samples, as reference the band at 1880±5 $cm^{-1}$ was taken.

Reference Example 2.7: Determination of Crystallinity Via XRD

The crystallinity of the zeolitic materials according to the present invention were determined by XRD analysis. The data were collected using a standard Bragg-Brentano diffractometer with a Cu—X-ray source and an energy dispersive point detector. The angular range of 2° to 70° (2 theta) was scanned with a step size of 0.02°, while the variable divergence slit was set to a constant illuminated sample length of 20 mm. The data were then analyzed using TOPAS V4 software, wherein the sharp diffraction peaks were modeled using a Pawley fit containing a unit cell with the following starting parameters: a=14.4 Angstrom (1 Angstrom=$10^{-10}$ m) and c=25.2 Angstrom in the space group P6/mmm. These were refined to fit the data. Independent peaks were inserted at the following positions: 8.4°, 22.4°, 28.2° and 43°. These were used to describe the amorphous content. The crystalline content describes the intensity of the crystalline signal to the total scattered intensity. Included in the model were also a linear background, Lorentz and polarization corrections, lattice parameters, space group and crystallite size.

Reference Example 3: Epoxidation Process

A main reactor A was a vertically mounted tube-bundle reactor with 5 tubes (length of the tubes: 12 m, internal tube diameter: 38 mm), each tube being equipped with an axially placed multipoint thermocouple with 10 equally spaced measuring points encased in a suitable thermowell with a diameter of 18 mm. Each tube was charged with 17.5 kg of the ZnTiMWW catalyst moldings as prepared according to Reference Example 1 (post-treated moldings). Free space eventually remaining was filled with steatite spheres (diameter of 3 mm). The heat of reaction was removed by circulating a thermostatized heat transfer medium (water/glycol mixture) on the shell side in co-current to the feed. The flow rate of the heat transfer medium was adjusted so that the temperature difference between entrance and exit did not exceed 1° C. The reaction temperature referred to hereinbelow, also referred to as $T^R$, was defined as the temperature of the heat transfer medium entering the reactor shell. At the reactor exit, the pressure was controlled by a pressure regulator and kept constant at 20 bar (abs). The output stream (5) leaving the epoxidation unit A was sampled every 20 minutes in order to determine the hydrogen peroxide concentration using the titanyl sulfate method and to calculate the hydrogen peroxide conversion. The hydrogen peroxide conversion was defined as $100 \times (1 - m_{out}/m_{in})$ wherein $m_{in}$ is the molar flow rate of $H_2O_2$ in the reactor feed and $m_{out}$ is the molar flow rate of $H_2O_2$ in the reactor outlet. Based on the respectively obtained hydrogen peroxide conversion values, the inlet temperature of the heat transfer medium was adjusted in order to keep the hydrogen peroxide conversion essentially constant in the range of from 90 to 92%. The inlet temperature of the heat transfer medium was set at 30° C. at the start of a given run with a fresh batch of the epoxidation catalyst and was increased, if necessary, to maintain the hydrogen peroxide conversion in the mentioned range. The required temperature increase was usually less than 1 K/d. The output stream (5) leaving the epoxidation unit A was passed through a heat exchanging unit. The stream leaving the heat exchanging unit (stream S) was fed to Epoxidation Unit B.

Epoxidation in a Finishing Reactor (Epoxidation Unit B): The finishing reactor B was a fixed bed reactor operated adiabatically. In this context, the term "adiabatic" refers to an operation mode according to which no active cooling is carried out and according to which the finishing reactor is suitably insulated in order to minimize heat losses. The finishing reactor B had a length of 4 m and a diameter of 100 mm. The reactor was filled with 9 kg of the same epoxidation catalyst which was used in the main epoxidation reactor A. Spare space was filled with steatite spheres (diameter of 3 mm). The operating pressure of the finishing reactor B was 10 bar which was kept constant by a suitable pressure regulator at the reactor exit. The output of the finishing reactor B was sampled every 20 min in order to determine the hydrogen peroxide concentration using the titanyl sulfate method. The effluent of the finishing reactor B, stream (6), was preferably depressurized into a flash drum, and both the liquid and the gas from this drum were fed to a light boiler separation column (distillation unit C).

The main reactor A was fed from below with a liquid monophasic stream (1). Stream (1) was prepared by mixing five streams (2), (2a), (3), (4) and (5). The temperature of stream (1) was in the range from 20 to 40° C. The streams were premixed at an absolute pressure of 23 bar. The liquid feed stream (1) consisted of one single liquid phase:

- Stream (2) was an acetonitrile stream and had a flow rate of 69 kg/h.
- Stream (2a) was a water stream and had a flow rate of 3 kg/h.
- Stream (3) having a flow rate of 12.9 kg/h was a propylene stream (containing 0.35 kg/h propene) and was supplied from a storage tank, allowing for a continuous feeding, and fed using a suitable metering pump.
- Stream (4) having a flow rate of 15 kg/h was an aqueous hydrogen peroxide solution having a hydrogen peroxide concentration of 40 weight-% ("crude/washed" grade from Solvay with a TOC in the range of 100 to 400 mg/kg). The aqueous hydrogen peroxide solution was supplied from a storage tank, allowing for a continuous feeding, and fed using a suitable metering pump.
- Stream (5) was an aqueous stream comprising dissolved potassium formate. The further stream was supplied from a storage tank, allowing for a continuous feeding, and was fed using a suitable metering pump. The concentration of the potassium formate was 2.5 weight-%, the feed rate of the stream was 500 g/h (1000 μmol potassium/mol hydrogen peroxide). Stream (5) was thoroughly mixed with stream (4) before the combined stream was mixed with the stream resulting from mixing streams (2), (2a) and (3).

The epoxidation was performed in a continuous manner.

The reactor effluent stream downstream the pressure control valve was collected, weighed and analyzed (effluent stream (6)). Organic components, with the exception of oxygen, were analyzed in two separate gas-chromatographs. The hydrogen peroxide content was determined colorimetrically using the titanyl sulfate method. Effluent stream (6) comprised 66.5 weight-% acetonitrile, 17.4 weight-% water, 11.6 weight-% propylene oxide, 3.8 weight-% propylene, 0.13 weight-% propylene glycol, 0.5 weight-% propane, 0.03 weight-% oxygen, 0.02 weight-% acetaldehyde, 0.01 weight-% propionaldehyde.

Reference Example 4: Separation of Propylene from Stream (6) to Obtain Stream S0

Separation of Light Boilers from Stream (6) to Obtain a Stream (8) (Stream S0)

Stream (6) was sent to a light boiler separation column (distillation unit C) operated at 1.1 bar. The distillation column had a length of 8.5 m, a diameter of 170 mm, and was equipped with 40 bubble trays, an evaporator at the bottom and a condenser at the top. The column was operated as a mixed washing/distillation tower. As a washing agent, part of the bottoms stream of distillation unit D (stream 11, about 20-30 kg/h) was taken off, cooled to 10° C. and introduced at the top of the column. Liquid and gaseous inlet streams were introduced to the column at different points. The feed point of the liquid portion of stream (6) was above bubble tray 37; the gaseous portion of stream (6) was introduced into the column above bubble tray 28 (counted from the top). The gaseous stream (7) leaving the column at the top contained mainly propene, propane (which was contained as impurity in the polymer-grade propene used), oxygen formed as a by-product and small amounts of other light boilers (acetonitrile (1-2 volume-%), propionaldehyde (about 200 volume-ppm), acetone (about 100 volume-ppm, $H_2$ (about 400 volume-ppm), $CO_2$ (about 400 volume-ppm) and acetaldehyde (about 100 volume-ppm)), and was essentially free of propylene oxide (less than 300 volume-ppm). This top stream was sent to the flare for disposal. Stream (8) (that is stream S0) was taken off of the light boiler separation column as bottoms stream.

Example 1: Separation of Propylene Oxide from Stream S0 to Obtain a Top Stream S1c Enriched in Propylene Oxide and a Bottoms Stream S1a Depleted of Carbonyl Compounds Stream S0 comprised acetonitrile (70.7 weight-%), water (18.9 weight-%), propylene oxide (10.1 weight-%), propionaldehyde (196 weight-ppm), acetaldehyde (145 weight-ppm), acetone (102 weight-ppm) and propylene glycol (0.21 weight-%) and was introduced into a first distillation column (distillation unit D) with 3.0 kg/h at a temperature of 40° C. and a pressure of 1 bar The column had a height of 8.1 m and a diameter of 5 mm and was equipped with a high-performance packing (Sulzer CY) with a packing of 3.6 m below the S0 feed point, 0.9 m packing between feed and side take-off and 3.6 m packing above the side take-off (counted from the bottom). The column was operated in continuous mode at a top pressure of 500 mbar and at a top temperature of 16° C. The overhead stream of the column was condensed and partly returned to the column as reflux (1200 g/h, reflux ratio approximately 4:1). A Stream S1b was taken off from the distillation unit D with 60 g/h via the side-take off by a dosing pump.

The amount of fed stream S0, the amount of stream S1b and the amount of the reflux were kept constant by flow controller. The amount of top stream S1c was taken off from the distillate container under level control. In order to regulate the energy supply to the sump, the average value of two temperature measuring points positioned between feed and side take off was taken as guidance value and was kept constant at 39° C. in that the temperature of the oil used for heating the sump boiler was adjusted.

Stream S1b contained propylene oxide (94 weight-%), propionaldehyde (1.0 weight-%), acetonitrile (4.5 weight-%), acetone (0.4 weight-%). The acetaldehyde content was less than 0.01 weight-%. The water content of S1b was not determined. Stream S1b was taken off from distillation unit D with 60 g/h via the side-take off by a dosing pump and mixed with a stream containing an aqueous hydrazine solution (3 weight-%, 10 g/h) in a static mixer. The resulting mixed stream had a molar ratio hydrazine:carbonyl compound of 0.6:1 and was conveyed to a tubular reactor. The reactor had a length of 0.28 m and a diameter of 10 mm. The temperature in the tubular reactor was adjusted to 60° C. by a double jacket with a circulating heat transfer medium therein. The temperature was controlled by thermostat.

The liquid stream leaving the reactor was then fed to the head of a second column (second distillation unit D2, second column D2). The second distillation unit D2 was a glass column with 30 mm diameter, equipped with a high-performance packing (Sulzer CY) with a packing height of 1.0 m (10 theoretical trays). Second column D2 was operated in continuous mode at a top pressure of 750 mbar and at a bottoms temperature of 38° C.

In order to regulate the second column D2, the amount of bottoms stream was taken off from the sump of D2 under level control. The temperature in the sump was taken as guiding value and kept constant at 38° C. in order to regulate the energy input in the sump. The temperature of the oil for the sump boiler was taken as controllable variable.

The gaseous top stream S3a from second column D2 was recycled to the first distillation column D via a feed positioned above the same theoretical tray as the side take-off.

The distillation was kept running until all compositions were stationary, especially the composition within the stream S1b, which was achieved after approximately 15 h. Thereafter, balancing was done over 6 hours.

The bottoms stream S3b from second column D2 had a red color and was discarded. No propylene oxide could be detected in S3b.

The top stream S1c was taken as overhead product from the first distillation unit D with 300 g/h and consisted of propylene oxide (99.8 weight-%) acetaldehyde (0.15 weight-%), water (50 weight-ppm), propionaldehyde (11 weight-ppm), acetonitrile (13 weight-ppm) and acetone (4 weight-ppm). The hydrazine content was <10 weight-ppm.

The stream S1a was taken as bottoms stream from the first distillation unit D with 2640 g/h and was free of ("free of"=content less than 50 wt.-ppm) propylene oxide, acetaldehyde, propionaldehyde, acetone, hydrazine and hydrazine derivatives. S1a had an acetonitrile content of about 80 weight-% and a water content of about 20 weight-%. Table 1 showed the compositions of streams S0, S1a, S1b and S1c.

TABLE 1 compositions of streams S0, S1a and S1c in Example 1.

| component | Stream S0 | Stream S1a | S1b | Stream S1c |
|---|---|---|---|---|
| propylene oxide | 10.1 weight-% | <50 weight-ppm | 94 weight-% | 99.8 weight-% |
| acetaldehyde | 145 weight-ppm | <50 weight-ppm | <0.01 weight-% | 0.15 weight-% |
| water | 18.9 weight-% | 20 weight-% | <1 weight-ppm | 50 weight-ppm |
| propionaldehyde | 196 weight-ppm | <50 weight-ppm | 1.0 weight-% | 11 weight-ppm |
| acetonitrile | 70.7 weight-% | 80 weight-% | 4.5 weight-% | 13 weight-ppm |
| acetone | 102 weight-ppm | <50 weight-ppm | 0.5 weight-% | 4 weight-ppm |
| Propylene glycol | 0.21 weight-% | 0.25 weight-% | <1 weight-ppm | <1 weight-ppm |
| Hydrazine | 0 | <50 weight-ppm | <1 weight-ppm | <10 weight-ppm |

"---": not determined

It could be observed that by taking a second stream from a first distillation unit, addition of an organic compound comprising an amino group —NH$_2$ (NH$_2$-compound), followed by distillation in a second column and recycling of a propylene oxide containing top stream from the second column to the first column, organic compounds comprising a carbonyl group, especially acetone and propionaldehyde, could be depleted to more than 99 weight-% without contaminating the acetonitrile containing bottoms stream from the first column with NH$_2$-compounds or their derivatives. The loss on propylene oxide was less than 0.02 weight-ppm in relation to the total weight of propylene oxide contained in S0. Acetaldehyde, which was not taken off with the stream S1b from the distillation unit D, could be separated easily later in a further distillation stage, whereby the amount of NH$_2$-compound could be minimized.

Example 2: Separation of Propylene Oxide from Stream S1b to Obtain a Top Stream S3a Enriched in Propylene Oxide and a Bottoms Stream S3b Depleted of Carbonyl Compounds In analogy to Example 1 a Stream S1b was fed to the head of a second column (second distillation unit D2, second column D2). Stream S1b contained acetaldehyde (420 weight-ppm), propylene oxide (78.1 weight-%), propionaldehyde (590 weight-ppm), acetonitrile (21.7 weight-%), acetone (390 ppm-%). Further, a hydrazine stream was added at the top of the second column D2. The second distillation unit D2 was a glass column with an inner diameter of 50 mm equipped with a high-performance packing made of stainless steel (Sulzer DX) with a packing height of 1.045 m (about 20 theoretical trays). Second column D2 was operated in a semi-continuous mode at a top pressure of 540 mbar and at a bottoms temperature of 59° C.

The bottom stream S3b was collected in the bottom pot of the glass column. The pot was heated electrically with a heating jacket providing constant energy input.

The gaseous top stream S3a from second column D2 was collected in glass flasks and analyzed.

The distillation was kept running until a stationary temperature profile was observed, which was achieved after approximately 20 min. Thereafter, the distillate stream S3a was collected in a fresh flask for about 20 min to do the mass balancing.

Table 2 shows the compositions, Table 3 the flow rates of streams S1b, S3a, S3b as well as of the stream comprising the NH$_2$ compound.

TABLE 2 compositions of the streams in Example 2

| component | S1b [weight-%] | S3a [weight-%] | S3b [weight-%] | NH$_2$ compound [weight-%] |
|---|---|---|---|---|
| acetaldehyde | 0.042 | 0.01 | 0 | 0 |
| propylene oxide | 78.1 | 95.0 | 2.8 | 0 |
| propionaldehyde | 0.06 | 0.01 | 0 | 0 |
| acetone | 0.04 | 0.02 | 0.09 | 0 |
| acetonitril | 21.76 | 3.56 | 83.1 | 0 |
| acetaldehyde-azin | 0 | 0 | 0.14 | 0 |
| propionaldehyde-azin | 0 | 0 | 0.23 | 0 |
| acetone azin | 0 | 0 | 0.02 | 0 |
| propylene glycol | 0 | 0 | 0 | 0 |
| hydrazine | 0 | 0 | 0.21 | 1.8 |
| water | 0 | 1.4 | 13.4 | 98.2 |
| Total | 100 | 100 | 100 | 100 |

TABLE 3 flow rates of the streams in Example 2

| component | S1b [g/h] | S3a [g/h] | S3b [g/h] | NH$_2$ compound [g/h] |
|---|---|---|---|---|
| acetaldehyde | 0.35 | 0.08 | 0 | 0 |
| propylene oxide | 660.7 | 655.3 | 5.3 | 0 |
| propionaldehyde | 0.50 | 0.06 | 0 | 0 |
| acetone | 0.33 | 0.11 | 0.18 | 0 |
| acetonitril | 183.6 | 24.9 | 158.6 | 0 |
| acetaldehyde-azin | 0 | 0 | 0.26 | 0 |
| propionaldehyde-azin | 0 | 0 | 0.42 | 0 |
| acetone azin | 0 | 0 | 0.04 | 0 |
| propylene glycol | 0 | 0 | 0 | 0 |
| hydrazine | 0 | 0 | 0.40 | 0.63 |
| water | 0 | 9.2 | 25.6 | 34.5 |
| Total Flow | 845.4 | 689.7 | 190.8 | 35.1 |

It could be observed that by distillation in a second column under addition of an organic compound comprising an amino group —$NH_2$ ($NH_2$-compound) to the second column, organic compounds comprising a carbonyl group (propionaldehyde, acetaldehyde and acetone) could be reduced in the top stream S3a by 55% to 89% in relation to their amount in stream S1b. The stream S3a was not contaminated with $NH_2$-compounds or their derivatives. The $NH_2$-compounds and their derivatives were found in the bottom stream S3b.

SHORT DESCRIPTION OF THE FIGURES

Figure 2:
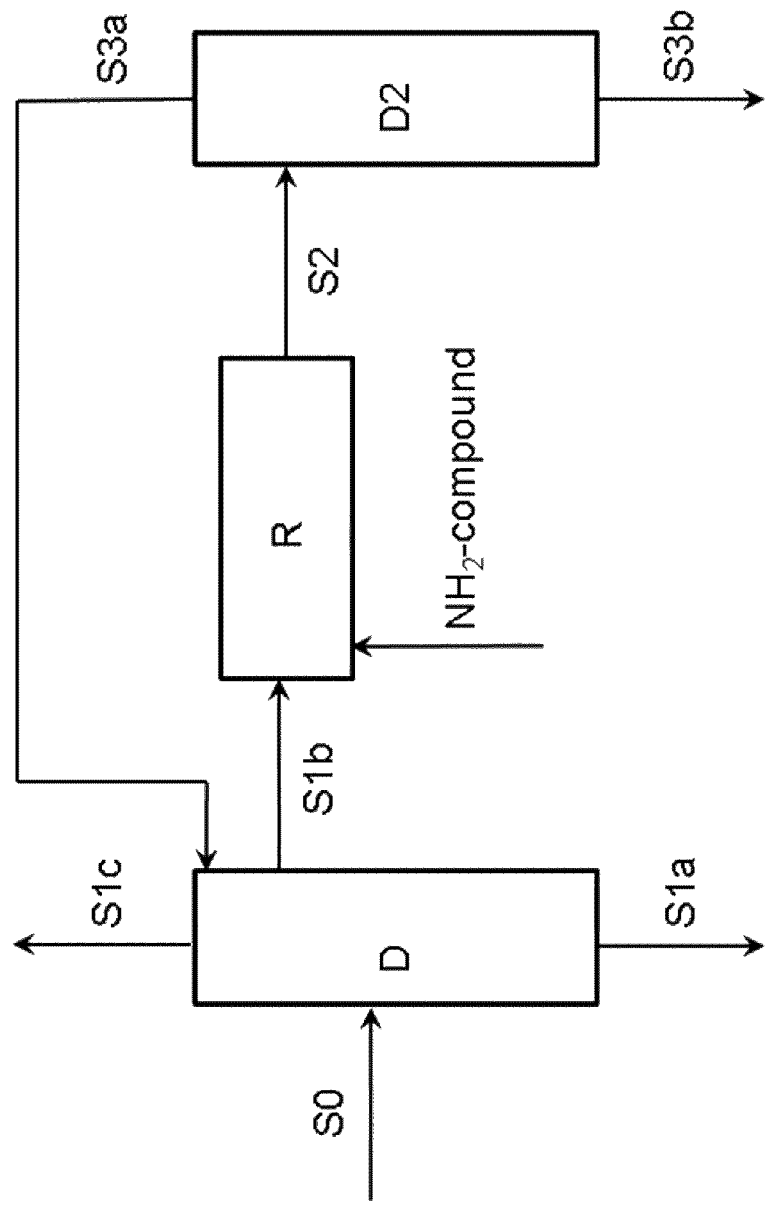

FIG. 1 shows a block diagram of the process according to Reference Examples 3 and 4 and Examples 1 and 2. In FIG. 1, the letters and numbers have the following meanings:
A epoxidation unit A
B epoxidation unit B
C distillation unit
D first distillation unit
D2 second distillation unit
(1)-(11) streams according to a specifically preferred process as described in the examples
S0, S1a, S1b, S1c, S3a, S3b streams according to a preferred process as described in the general description and the examples FIG. 2 shows a block diagram of the distillation units D and D2 from FIG. 1 in detail for Example 1. In FIG. 2, the letters and numbers have the following meanings:
D first distillation unit
D2 second distillation unit
R reactor
NH2-compound organic compound comprising an amino group —$NH_2$
S0, S1a, Sib, S1c, S2, S3a, S3b streams according to a specifically preferred process as described in the general description and in Example 1

Figure 3:
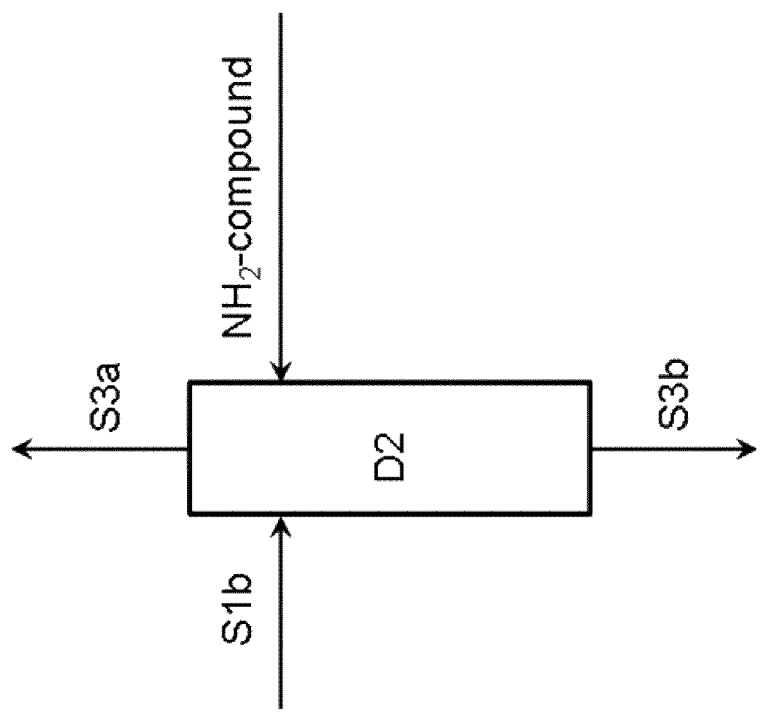

FIG. 3 shows a block diagram of the distillation unit D2 from FIG. 1 in detail for Example 2. In FIG. 3, the letters and numbers have the following meanings:
D2 second distillation unit
NH2-compound organic compound comprising an amino group —$NH_2$
S1b, S3a, S3b streams according to a specifically preferred process as described in the general description and in Example 2

CITED LITERATURE

EP 0 004 019 A2
WO 2011/123541 A1
Ullmann's Encyclopedia of Industrial Chemistry, 5th edition, volume A 13 (1989) pages 443-466
EP 1 122 249 A1

The invention claimed is:
1. A process for purifying propylene oxide, the process comprising
(i) providing a stream S0 comprising propylene oxide, acetonitrile, water, and an organic compound comprising a carbonyl group —C(=O)—, wherein said organic compound comprising a carbonyl group —C(=O)— comprises one or more of acetone and propionaldehyde; and
(ii) separating propylene oxide from the stream S0 by distillation by
(ii.1) subjecting the stream S0 to distillation conditions in a first distillation unit, obtaining a gaseous top stream S1c which is enriched in propylene oxide compared to the stream S0, a liquid bottoms stream S1a which is enriched in acetonitrile and water compared to the stream S0, and a side stream S1b comprising propylene oxide which is enriched in the carbonyl compound compared to the stream S0;
(ii.2) reacting the carbonyl compound comprised in the side stream S1b with an organic compound comprising an amino group —$NH_2$ obtaining a reaction product of the organic compound comprising a carbonyl group and the organic compound comprising an amino group;
(ii.3) separating propylene oxide from the reaction product of the organic compound comprising a carbonyl group and the organic compound comprising an amino group in a second distillation unit, obtaining a gaseous top stream S3a which is enriched in propylene oxide and a liquid bottoms stream S3b which is enriched in the reaction product of the organic compound comprising a carbonyl group and the organic compound comprising an amino group; and
(ii.4) introducing the top stream S3a which is enriched in propylene oxide propylene oxide into the first distillation unit.

2. A process for purifying propylene oxide, the process comprising
(i) providing a stream S0 comprising propylene oxide, acetonitrile, water, and an organic compound comprising a carbonyl group —C(=O)—, wherein said organic compound comprising a carbonyl group —C(=O)— comprises one or more of acetone and propionaldehyde; and
(ii) separating propylene oxide from the stream S0 by distillation by
(ii.1) subjecting the stream S0 to distillation conditions in a first distillation unit, obtaining a gaseous top stream S1c which is enriched in propylene oxide compared to the stream S0, a liquid bottoms stream S1a which is enriched in acetonitrile and water compared to the stream S0, and a side stream S1b comprising propylene oxide which is enriched in the carbonyl compound compared to the stream S0;
(ii.2) admixing the side stream S1b with an organic compound comprising an amino group —$NH_2$ and reacting the organic compound comprising a carbonyl group with the organic compound comprising an amino group, obtaining a stream S2 comprising propylene oxide and a reaction product of the organic compound comprising a carbonyl group and the organic compound comprising an amino group;
(ii.3) subjecting the stream S2 to distillation conditions in a second distillation unit, obtaining a gaseous top stream S3a which is enriched in propylene oxide compared to the stream S2, and a liquid bottoms stream S3b which is enriched in the reaction product of the organic compound comprising a carbonyl group and the organic compound comprising an amino group compared to the stream S2; and
(ii.4) introducing the stream S3a into the first distillation unit.

3. A process for purifying propylene oxide, the process comprising
(i) providing a stream S0 comprising propylene oxide, acetonitrile, water, and an organic compound comprising a carbonyl group —C(=O)—, wherein said organic compound comprising a carbonyl group —C(=O)— comprises one or more of acetone and propionaldehyde; and (ii) separating propylene oxide from the stream S0 by distillation by
  (ii.1) subjecting the stream S0 to distillation conditions in a first distillation unit, obtaining a gaseous top stream S1c which is enriched in propylene oxide compared to the stream S0, a liquid bottoms stream S1a which is enriched in acetonitrile and water compared to the stream S0, and a side stream S1b comprising propylene oxide which is enriched in the carbonyl compound compared to the stream S0;
  (ii.2) subjecting the side stream S1b to distillation conditions in a second distillation unit and adding an organic compound comprising an amino group —$NH_2$ to the second distillation unit, and reacting the organic compound comprising a carbonyl group with the organic compound comprising an amino group, obtaining a reaction product of the organic compound comprising a carbonyl group and the organic compound comprising an amino group, and obtaining a gaseous top stream S3a which is enriched in propylene oxide compared to the stream S1b, and a liquid bottoms stream S3b which is enriched in the reaction product of the organic compound comprising a carbonyl group and the organic compound comprising an amino group compared to the stream S1b; and
  (ii.3) introducing the stream S3a into the first distillation unit.

4. The process of claim 1, wherein the organic compound comprising a carbonyl group —C(=O)— comprised in the stream S0 further comprises one or more of acetaldehyde, formaldehyde, butyraldehyde, isobutyraldehyde, 2-butanon, 1-pentanal, 2-pentanon, 3-pentanon, and 2-methylpentanone.

5. The process of claim 1, wherein at least 95 weight % of the stream S0 consist of propylene oxide, acetonitrile, water, and the organic compound comprising a carbonyl group.

6. The process of claim 1, wherein the stream S0 is obtained by a process comprising
  (a) providing a liquid feed stream comprising propene, hydrogen peroxide, water, and acetonitrile;
  (b) passing the liquid feed stream provided in (a) into an epoxidation zone comprising an epoxidation catalyst comprising a titanium zeolite, and subjecting the liquid feed stream to epoxidation reaction conditions in the epoxidation zone, obtaining a reaction mixture comprising propene, propylene oxide, water, acetonitrile, and the organic compound comprising a carbonyl group;
  (c) removing an effluent stream from the epoxidation zone, the effluent stream comprising propylene oxide, water, acetonitrile, propene, and the organic compound comprising a carbonyl group;
  (d) separating propene from the effluent stream by distillation by subjecting the effluent stream to distillation conditions in a distillation unit, obtaining a gaseous stream which is enriched in propene compared to the effluent stream subjected to distillation conditions, and a liquid bottoms stream which is enriched in propylene oxide, water, acetonitrile and the organic compound comprising a carbonyl group compared to the effluent stream subjected to distillation conditions;
  wherein said liquid bottoms stream obtained in (d) is the stream S0.

7. The process of claim 1, wherein said providing (i) comprises
  (a) providing a liquid feed stream comprising propene, hydrogen peroxide, water, and acetonitrile;
  (b) passing the liquid feed stream provided in (a) into an epoxidation zone comprising an epoxidation catalyst comprising a titanium zeolite, and subjecting the liquid feed stream to epoxidation reaction conditions in the epoxidation zone, obtaining a reaction mixture comprising propene, propylene oxide, water, acetonitrile, and the organic compound comprising a carbonyl group;
  (c) removing an effluent stream from the epoxidation zone, the effluent stream comprising propylene oxide, water, acetonitrile, propene, and the organic compound comprising a carbonyl group;
  (d) separating propene from the effluent stream by distillation by subjecting the effluent stream to distillation conditions in a distillation unit, obtaining a gaseous stream which is enriched in propene compared to the effluent stream subjected to distillation conditions, and a liquid bottoms stream which is enriched in propylene oxide, water, acetonitrile and the organic compound comprising a carbonyl group compared to the effluent stream subjected to distillation conditions;
  wherein said liquid bottoms stream obtained in (d) is the stream S0.

8. The process of claim 1, wherein the first distillation unit employed in (ii.1) is at least one distillation tower.

9. The process of claim 1, wherein a rectifying section of the first distillation unit employed in (ii.1) consists of from 40 to 60% of theoretical trays and a stripping section of the distillation unit consists of from 60 to 40% of theoretical trays.

10. The process of claim 1, wherein the first distillation unit employed in (ii.1) is operated at a top pressure of from 0.1 to 2.0 bar.

11. The process of claim 1, wherein the first distillation unit employed in (ii.1) is operated at a top temperature in the range of from 50 to 70° C.

12. The process of claim 1, wherein the first distillation unit employed in (ii.1) is operated at an internal reflux ratio in the range of from 1 to 10.

13. The process of claim 1, wherein the side stream S1b obtained in (ii.1) is removed from a rectifying section of the first distillation unit.

14. The process of claim 1, wherein the side stream S1b obtained in (ii.1) is removed from a rectifying section of the first distillation unit at a position which is at least 1 theoretical tray above a stripping section of the first distillation unit.

15. The process of claim 1, wherein the side stream S1b obtained in (ii.1) is removed from a rectifying section of the first distillation unit at a position which is from 1 to 15 theoretical tray above a stripping section of the first distillation unit.

16. The process of claim 1, wherein the organic compound comprising an amino group —$NH_2$ comprises one or more of R—$NH_2$, wherein R is a substituted or unsubstituted, branched or unbranched C1-C5-alkyl; R1-$NH_2$, wherein R1 is a C6-C10-aryl group with at least one further substituent R2 selected from the group consisting of hydrogen, —$CH_3$, and —$NO_2$ positioned at the aryl group; $NH_2$—R3-$NH_2$, wherein R3 is selected from the group consisting of a C2-C3-alkylene group and a phenyl group a N-C1-C6-aminale; a carbonic acid amide an amide of mono-methylester of methylphosphonic acid; an amide of a carbonic acid;

an amino acid; anthranilic acid; a nitrile of an alpha-amino carbonic acid; cyanamide; hydroxylamine; O-methylhydroxylamine; hydroxylamine-O-sufonic acid; hydrazine; hydrazine monohydrate; a monoC1-C4-alkyl hydrazine; an aryl hydrazine a dialkyl hydrazine; a hydrazide; and a hydrazide of a thiocarbonic acid of formula $R4(S=O)_2-NH-NH_2$ wherein R4 is selected from the group consisting of C6-C10-aryl and C1-C6-alkyl.

17. The process of claim 1, wherein said reacting (ii.2) is carried out in one or more reactors.

18. The process of claim 1, wherein the second distillation unit employed in (ii.3) is at least one distillation towel.

19. The process of claim 1, wherein the gaseous top stream S3a obtained in (ii.3) is introduced into the first distillation unit in (ii.4) in a rectifying section of the first distillation unit at a position which is at least 1 theoretical tray above a stripping section of the first distillation unit.

20. The process of claim 1, wherein the gaseous top stream S3a obtained in (ii.3) is introduced into the first distillation unit in (ii.4) in a rectifying section of the first distillation unit at a position which is 0 to 3 theoretical trays above the theoretical tray where the side stream S1b obtained in (ii.1) is removed from the rectifying section of the first distillation.

21. The process of claim 1, which is a continuous process.

* * * * *

UNITED STATES PATENT AND TRADEMARK OFFICE
CERTIFICATE OF CORRECTION

PATENT NO.        : 10,676,451 B2
APPLICATION NO.   : 16/315345
DATED             : June 9, 2020
INVENTOR(S)       : Joaquim Henrique Teles et al.

It is certified that error appears in the above-identified patent and that said Letters Patent is hereby corrected as shown below:

In the Specification

Column 4, Line 61, "one ore more" should read -- one or more --.

Column 6, Line 30, "one ore more" should read -- one or more --; and
Line 51, "acealdehyde" should read -- acetaldehyde --.

Column 7, Line 24, "hydroxylamine-O-sufonic acid" should read -- hydroxylamine-O-sulfonic acid --; and
Line 25, "monoC1-C4-alkyl" should read -- mono-C1-C4-alkyl --.

Column 10, Line 7, "Sic," should read -- S1c, --; and
Line 9, "Sic." should read -- S1c. --.

Column 11, Line 6, "and and" should read -- and --.

Column 14, Line 59, "of of hydrogen" should read -- of hydrogen --.

Column 17, Line 53, "one ore more" should read -- one or more --; and
Line 62, "one ore more" should read -- one or more --.

Column 18, Line 44, "and and the" should read -- and the --.

Column 19, Line 6, "and and the" should read -- and the --.

Column 20, Line 22, "Sib," should read -- S1b, --;
Line 25, "acealdehyde" should read -- acetaldehyde --;
Line 27, "Sib." should read -- S1b. --;
Line 57, "hydroxylamine-O-sufonic acid" should read -- hydroxylamine-O-sulfonic acid --; and Signed and Sealed this
Fifteenth Day of September, 2020

Andrei Iancu
*Director of the United States Patent and Trademark Office*

CERTIFICATE OF CORRECTION (continued)
U.S. Pat. No. 10,676,451 B2

Line 58, "monoC1-C4-alkyl" should read -- mono-C1-C4-alkyl --.

Column 22, Line 1, "theorectical" should read -- theoretical --.

Column 25, Line 12, "90 g/I" should read -- 90 g/l --; and
    Line 20, "(Horward-Kawazoe method)" should read -- (Horvath-Kawazoe method) --.

Column 26, Line 17, "mulitpoint" should read -- multipoint --;
    Line 28, "deioinized" should read -- deionized --; and
    Line 43, "332 g/I" should read -- 332 g/l --.

Column 27, Line 34, "Tr/4" should read -- $\pi/4$ --; and
    Line 54, "Prüfmaschine" should read -- Prüfmaschinen --.

Column 31, Line 65, "(acetonitrile (1-2 volume-%)," should read -- acetonitrile (1-2 volume-%), --.

Column 33, Line 22, "Sic." should read -- S1c. --.

Column 34, Line 23, "Sib," should read -- S1b, --;
    Line 37 (approx.), "acetonitril" should read -- acetonitrile --; and
    Line 57 (approx.), "acetonitril" should read -- acetonitrile --.

Column 35, Line 3, "acetonaldehyde" should read -- acetaldehyde --;
    Line 24, "examples" should read -- examples. --;
    Line 31, "NH2-compound" should read -- $NH_2$-compound --; and
    Line 33, "Sib," should read -- S1b, --;

Column 35, Line 35, "Example 1" should read -- Example 1. --;
    Line 40, "NH2-compound" should read -- $NH_2$-compound --; and
    Line 44, "Example 2" should read -- Example 2. --.

In the Claims

Column 36, Line 22, Claim 1, "propylene oxide propylene oxide" should read -- propylene oxide --.

Column 37, Line 37 (approx.), Claim 5, "weight %" should read -- weight-% --.

Column 38, Line 65, Claim 16, "phenyl group" should read -- phenyl group; --; and
    Line 66, Claim 16, "acid amide" should read -- acid amide; --.

Column 39, Line 3, Claim 16, "hydroxylamine-O-sufonic acid;" should read -- hydroxylamine-O-sulfonic acid; --; and
    Line 4, Claim 16, "monoC1-C4-alkyl" should read -- mono-C1-C4-alkyl --.

Column 39, Line 5, Claim 16, "aryl hydrazine" should read -- aryl hydrazine; --; and
    Line 12, Claim 18, "towel." should read -- tower. --.